(12) United States Patent
Hosokawa et al.

(10) Patent No.: US 8,044,390 B2
(45) Date of Patent: Oct. 25, 2011

(54) MATERIAL FOR ORGANIC ELECTROLUMINESCENT DEVICE, ORGANIC ELECTROLUMINESCENT DEVICE, AND ORGANIC ELECTROLUMINESCENT DISPLAY

(75) Inventors: Chishio Hosokawa, Sodegaura (JP); Hironobu Morishita, Sodegaura (JP); Tadahiko Yoshinaga, Tokyo (JP); Yasunori Kijima, Tokyo (JP)

(73) Assignees: Idemitsu Kosan Co., Ltd., Tokyo (JP); Sony Corporation, Tokyo (JP)

( * ) Notice: Subject to any disclaimer, the term of this patent is extended or adjusted under 35 U.S.C. 154(b) by 131 days.

(21) Appl. No.: 12/601,808

(22) PCT Filed: May 21, 2007

(86) PCT No.: PCT/JP2008/059303
§ 371 (c)(1),
(2), (4) Date: Dec. 17, 2009

(87) PCT Pub. No.: WO2008/146665
PCT Pub. Date: Dec. 4, 2008

(65) Prior Publication Data
US 2010/0181555 A1    Jul. 22, 2010

(30) Foreign Application Priority Data
May 25, 2007    (JP) .................. 2007-138870

(51) Int. Cl.
*H01L 51/00*    (2006.01)
(52) U.S. Cl. .................. 257/40; 257/103; 257/E51.026; 257/E51.028; 549/59; 544/345
(58) Field of Classification Search ............ 257/40, 257/103, E51.026, E51.028; 549/59; 544/345
See application file for complete search history.

(56) References Cited

U.S. PATENT DOCUMENTS
4,720,432 A    1/1988  VanSlyke et al.
(Continued)

FOREIGN PATENT DOCUMENTS
JP    60-115575 A    6/1985
(Continued)

OTHER PUBLICATIONS
T. Suzuki, Single-Component Organic Semiconductors Based on Novel Radicals that Exhibit Electrochemical Amphotericity: Preparation, Crystal Structures, and Solid-State Properties of N, N'-Dicyanopyrazinonaphathoquinodiiminides Substitute with an N-Alkylpyridiminum Unit, Journal of Organic Chemistry, Jan. 12, 2001, vol. 66, No. 1, pp. 216-224.
(Continued)

Primary Examiner — Tu-Tu Ho
(74) Attorney, Agent, or Firm — Foley & Lardner LLP

(57) ABSTRACT

A material for an organic electroluminescent device including an imine derivative represented by the following formula (Ia) or (Ib),

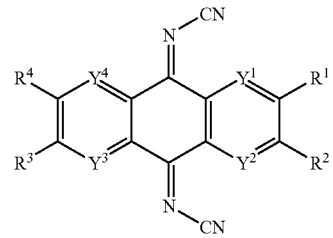

(Ia)

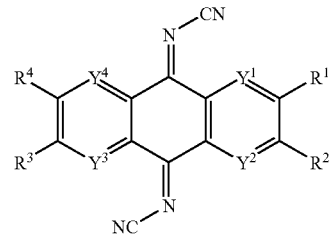

(Ib)

wherein $Y^1$ to $Y^4$ are independently a carbon atom or a nitrogen atom; $R^1$ to $R^4$ are independently hydrogen, an alkyl group, an aryl group, a heterocycle, a halogen atom, a fluoroalkyl group or a cyano group; and $R^1$ and $R^2$, or $R^3$ and $R^4$ may be bonded together to form a ring.

16 Claims, 3 Drawing Sheets

U.S. PATENT DOCUMENTS

| | | | |
|---|---|---|---|
| 5,061,569 A | 10/1991 | VanSlyke et al. | |
| 5,077,142 A | 12/1991 | Sakon et al. | |
| 7,538,341 B2 * | 5/2009 | Son et al. | 257/40 |
| 2004/0113547 A1 | 6/2004 | Son et al. | |
| 2005/0255334 A1 | 11/2005 | Kang et al. | |
| 2007/0090756 A1 | 4/2007 | Okada et al. | |

FOREIGN PATENT DOCUMENTS

| | | | |
|---|---|---|---|
| JP | 62-032465 A | 2/1987 |
| JP | 02-042449 A | 2/1990 |
| JP | 02-214866 A | 8/1990 |
| JP | 04-297076 A | 10/1992 |
| JP | 09-003342 A | 1/1997 |
| JP | 11-251067 A | 9/1999 |
| JP | 2000-109717 A | 4/2000 |
| JP | 2000-196140 A | 7/2000 |
| JP | 2001-297883 A | 10/2001 |
| JP | 2003-031365 A | 1/2003 |
| JP | 2004-514257 A | 5/2004 |
| JP | 2005-167175 A | 6/2005 |

OTHER PUBLICATIONS

C.W. Tang et al., Organic Electroluminescent Diodes, Applied Physics Letters, Sep. 21, 1987, vol. 51, No. 12, pp. 913-915.

* cited by examiner (A)

(B)

US 8,044,390 B2

MATERIAL FOR ORGANIC ELECTROLUMINESCENT DEVICE, ORGANIC ELECTROLUMINESCENT DEVICE, AND ORGANIC ELECTROLUMINESCENT DISPLAY

CROSS REFERENCE TO RELATED APPLICATION

This is the U.S. national phase application under 35 U.S.C. §371 of International Patent Application No. PCT/JP2008/059303, filed May 21, 2008, which claims the benefit of Japanese Application No. 2007-138870, filed May 25, 2007. The International Application was published on Dec. 4, 2008 as International Publication No. WO/2008/146665 published in the Japanese language under PCT Article 21(2). The contents of these applications are incorporated by reference herein in their entireties.

TECHNICAL FIELD

The invention relates to a material for an organic electroluminescent device, an organic electroluminescent device using the same, and an organic electroluminescent display device.

BACKGROUND ART

An organic electroluminescence device (hereinafter the term "electroluminescent" is often abbreviated as "EL") is a self-emission device utilizing the principle that a fluorescent compound emits light by the recombination energy of holes injected from an anode and electrons injected from a cathode when an electric field is impressed.

Since C. W. Tang et al. of Eastman Kodak Co. reported a low-voltage driven organic EL device of stack type (Non-patent Document 1, or the like), studies on organic EL devices wherein organic materials are used as the constituent materials has actively been conducted.

The organic EL device reported by Tang et al. has a stack structure in which tris(8-hydroxyquinolinol)aluminum is used in an emitting layer and a triphenyldiamine derivative is used in a hole-transporting layer. The advantages of the stack structure are to increase injection efficiency of holes to the emitting layer, to increase generation efficiency of excitons generated by recombination by blocking electrons injected in the cathode, to confine the generated excitons in the emitting layer, and so on.

As the stack structure of the organic EL device, a two-layered type of a hole-transporting (injecting) layer and an electron-transporting emitting layer, and a three-layered type of a hole-transporting (injecting) layer, an emitting layer and an electron-transporting (injecting) layer are widely known. In such stack structure devices, their device structures and fabrication methods have been contrived to increase recombination efficiency of injected holes and electrons.

As a hole-transporting material used in an organic EL device, an aromatic diamine derivative described in Patent Document 1 and an aromatic condensed-ring diamine derivative described in Patent Document 2 have been known.

However, in order that an organic EL device using these aromatic diamine derivatives as a hole-transporting material has a sufficient luminance, it is necessary to increase an applied voltage. The increased voltage results in problems such as the shorter device lifetime and higher power consumption.

As a solution thereof, it is proposed that a hole-injecting layer of an organic EL device is doped with a electron-accepting compound such as a Lewis acid (Patent Documents 3 to 8, etc.). However, electron-accepting compounds used in Patent Documents 3 to 6 have the following disadvantages. They are unstable when handling during the production of an organic EL device, or they lack stability such as heat resistance, thereby shortening the lifetime of the resultant device.

Tetrafluorotetracyanoquinodimethane ($TCNQF_4$), which is an electron-accepting compound exemplified in Patent Documents 5 and 7 to 9, is easily sublimated due to its small molecular weight, and being substituted with fluorine. Thus, they may scatter in an apparatus during the production of an organic EL device by vacuum deposition, resulting in contamination of the apparatus and device.

The invention was made in view of the problems mentioned above, and an object of the invention is to provide an electron-accepting material suitable for a constituent material of an EL device.

Patent Document 1: U.S. Pat. No. 4,720,432
Patent Document 2: U.S. Pat. No. 5,061,569
Patent Document 3: JP-A-2003-031365
Patent Document 4: JP-A-2001-297883
Patent Document 5: JP-A-2000-196140
Patent Document 6: JP-A-H11-251067
Patent Document 7: JP-A-H4-297076
Patent Document 8: JP-T-2004-514257
Patent Document 9: US 2005/0255334A1
Non-Patent Document 1: Applied Physics, Letters, 51, 913 (1987)

SUMMARY OF THE INVENTION

As a result of the studies, the inventors have paid attention to compounds having a dipyrazino skeleton. These compounds have a skeleton similar to anthraquinone and a resonant system spreading over a ring. Therefore, it is known by ESR measurement or electrochemical measurement that their anion radical is stable (Z. Naturforsch, vol. 46b, pages 326 to 338, J. Am. Chem. Soc., vol. 85, page 1821, etc.). In addition, the compounds are excellent in heat resistance, whereby they are expected to have deposition stability during the production of a device and to suppress heat deterioration when a device is drived.

As a result of the further studies, the inventors found that if specific compounds among the above-mentioned compounds have the imine type structure of the invention, they can be an electron-accepting material suitable for an organic EL device, and a device can be produced by purifying the compounds by sublimation or depositing the compounds due to their improved heat resistance. The inventors also found that the compounds with such properties can realize lower driving voltage and longer lifetime of the organic EL device using these.

According to the invention, the following material for an organic EL device and the like can be provided.

1. A material for an organic electroluminescent device comprising an imine derivative represented by the following formula (Ia) or (Ib),

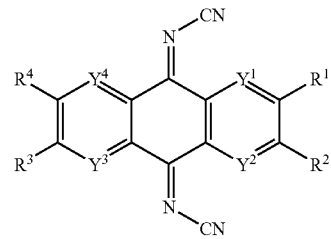

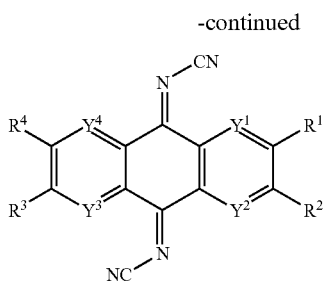

wherein $Y^1$ to $Y^4$ are independently a carbon atom or a nitrogen atom; $R^1$ to $R^4$ are independently hydrogen, an alkyl group, an aryl group, a heterocycle, a halogen atom, a fluoroalkyl group or a cyano group; and $R^1$ and $R^2$, or $R^3$ and $R^4$ may be bonded together to form a ring.

2. The material for an organic electroluminescent device according to 1 wherein the imine derivative is represented by the following formula (IIa) or (IIb),

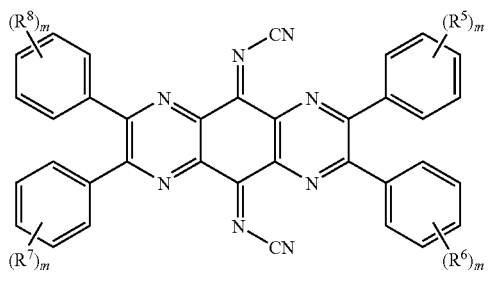

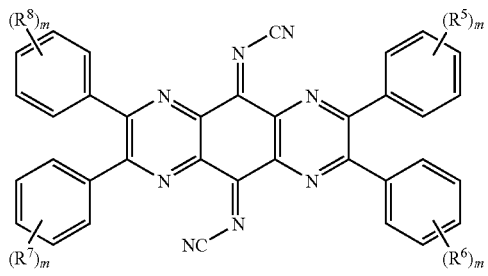

wherein $R^5$ to $R^8$ are independently hydrogen, an alkyl group, fluorine, a fluoroalkyl group or a cyano group; provided that at least one of $R^5$ to $R^8$ is fluorine or a fluoroalkyl group; and ms are independently an integer of 1 to 5.

3. The material for an organic electroluminescent device according to 1 or 2 wherein the reduction potential of an acetonitrile solution is −1.0V (vs Fc$^+$/Fc wherein Fc represents ferrocene) or more.

4. The material for an organic electroluminescent device according to any one of 1 to 3 which is a hole-injecting material.

5. An organic electroluminescent device comprising an organic layer between an anode and a cathode wherein the organic layer comprises the material for an organic electroluminescent device according to any one of 1 to 4.

6. An organic electroluminescent device comprising an organic layer between an anode and a cathode,
wherein the organic layer is a thin-layer stack comprising a hole-injecting layer, a hole-transporting layer, an emitting layer and an electron-transporting layer in sequential order from the anode; and
the hole-injecting layer comprises the material for an organic electroluminescent device according to any one of 1 to 4.

7. The organic electroluminescent device according to 6 wherein the hole-injecting layer further comprises a phenylenediamine compound represented by the following formula (III);

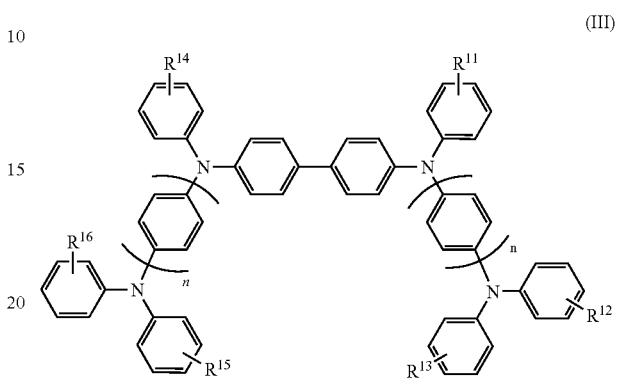

wherein $R^{11}$ to $R^{16}$ are independently hydrogen, a halogen atom, a trifluoromethyl group, an alkyl group, an aryl group or a heterocycle; $R^{11}$ to $R^{16}$ may each form a naphthalene skeleton, a carbazole skeleton, or a fluorene skeleton with its bonding phenyl group; and n represents 1 or 2.

8. The organic electroluminescent device according to 5 or 6 wherein the anode comprises a metal formed of aluminum or an aluminum alloy.

9. The organic electroluminescent device according to 8 wherein the anode comprises a stack of the metal formed of aluminum or an aluminum alloy, and a metal oxide or nitride.

10. An imine derivative represented by the following formula (IIa) or (IIb),

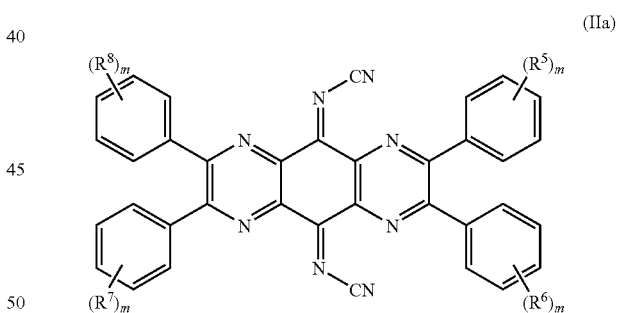

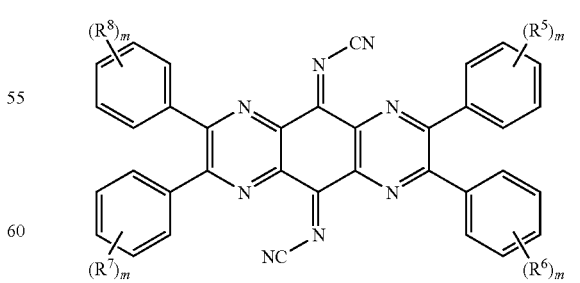

wherein $R^5$ to $R^8$ are independently hydrogen, an alkyl group, fluorine, a fluoroalkyl group or a cyano group; provided that at least one of $R^5$ to $R^8$ is a fluorine or a fluoroalkyl group; and ms are independently an integer of 1 to 5.

11. An organic electroluminescent display wherein a plurality of organic electroluminescent devices in which an anode, an organic layer comprising an emitting layer and a transparent cathode are stacked in sequential order are arranged on a substrate, and the organic layer comprises an imine derivative represented by the following formula (Ia) or (Ib),

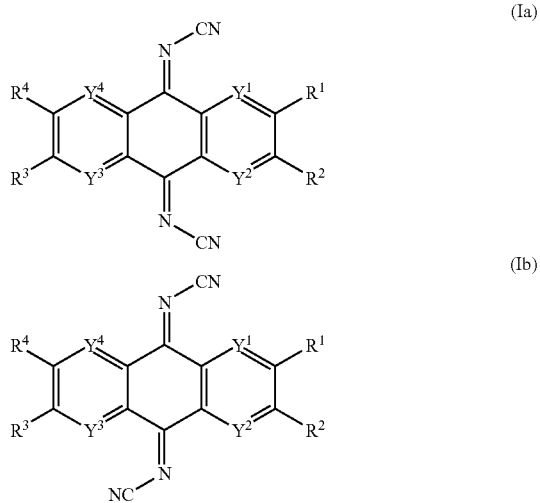

wherein $Y^1$ to $Y^4$ are independently a carbon atom or a nitrogen atom; $R^1$ to $R^4$ are independently hydrogen, an alkyl group, an aryl group, a heterocycle, a halogen atom, a fluoroalkyl group or a cyano group; and $R^1$ and $R^2$, or $R^3$ and $R^4$ may be bonded together to form a ring.

12. An organic electroluminescent display wherein a plurality of organic electroluminescent devices in which an anode, an organic layer comprising an emitting layer and a transparent cathode are stacked in sequential order are arranged on a substrate, and the organic layer comprises an imine derivative represented by the following formula (IIa) or (IIb),

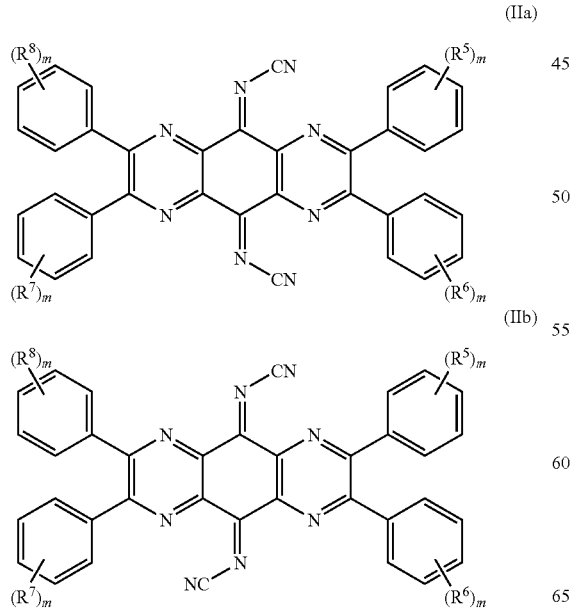

wherein $R^5$ to $R^8$ are independently hydrogen, an alkyl group, fluorine, a fluoroalkyl group or a cyano group; provided that at least one of $R^5$ to $R^8$ is a fluorine or a fluoroalkyl group; and ms are independently an integer of 1 to 5.

13. The organic electroluminescent display according to 11 or 12 wherein the anode comprises a metal formed of aluminum or an aluminum alloy.

14. The organic electroluminescent display according to 13 wherein the anode comprises a stack of the metal formed of aluminum or an aluminum alloy, and a metal oxide or nitride.

According to the invention, a novel material for an organic EL device can be provided. Further, a long-lifetime organic EL device which can be driven at a lower voltage can be provided.

BEST MODE FOR CARRYING OUT THE INVENTION

Figure 1:
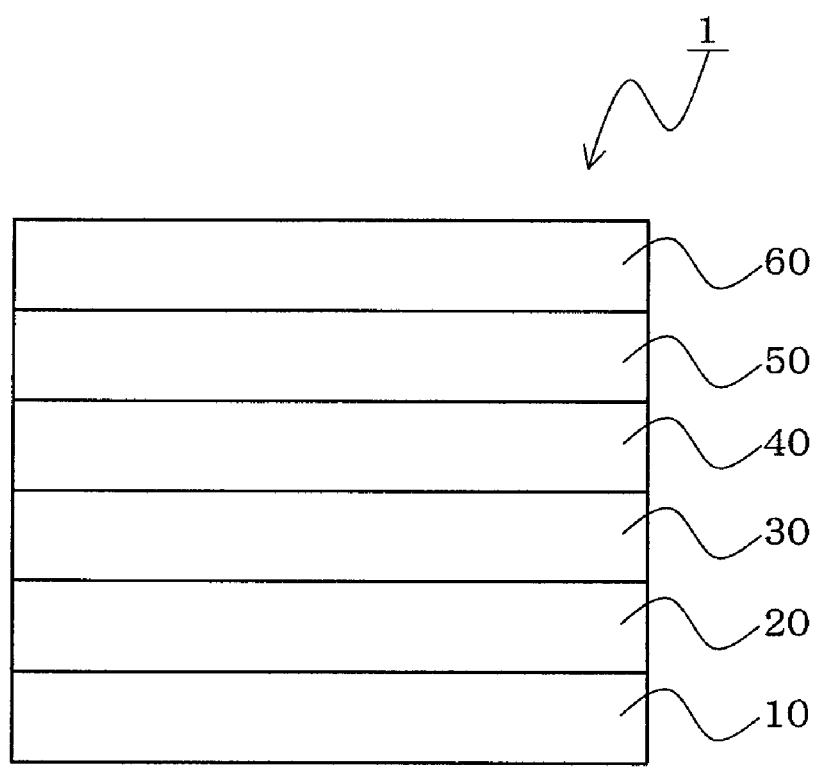
FIG. 1 is a schematic sectional view showing one embodiment of the organic EL device according to the invention.

The material for an organic EL device of the invention will be described.

The material for an organic EL device of the invention includes an imine derivative represented by the following formula (Ia) or (Ib)

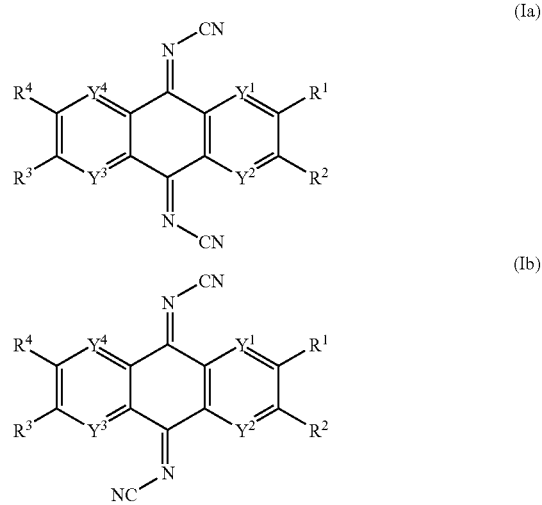

wherein $Y^1$ to $Y^4$ are independently a carbon atom or a nitrogen atom; $R^1$ to $R^4$ are independently hydrogen, an alkyl group, an aryl group, a heterocycle, a halogen atom, a fluoroalkyl group or a cyano group; and $R^1$ and $R^2$, or $R^3$ and $R^4$ may be bonded together to form a ring.

These structures can enhance the stability such as heat resistance and sublimation properties, and electron acceptability of a compound. This compound has an electron acceptability. The compound excels in heat resistance and can be purified by sublimation whereby the compound can be highly purified. When using in an organic EL device, the device can be driven at a low voltage and the lifetime thereof can be prolonged. In addition, since the compound does not scatter in a film-forming apparatus during the production of an organic EL device, the apparatus or the organic EL device is not contaminated.

Therefore, the compound is preferable as a material for an organic EL device, particularly a hole-injecting material.

Formulas (Ia) and (Ib) show syn type and anti type, respectively, i.e., isomers different in bonding positions of the cyano groups of two cyanoimine groups. The material of the invention is not limited to the specific isomers, and may contain syn type, anti type or a mixture thereof. Hereinafter, the "formulas (Ia) and (Ib)" is often abbreviated as "formula (I)". The same applies for formula (II) described later.

In formula (I), as the alkyl group of $R^1$ to $R^4$, a linear or branched alkyl group having 1 to 20 carbon atoms and cycloalkyl group having 3 to 20 ring carbon atoms are preferable. For example, a methyl group, ethyl group, n-propyl group, isopropyl group, n-butyl group, sec-butyl group, tert-butyl group, cyclopentyl group, cyclohexyl group, cycro heptyl group, adamantyl group and the like can be given.

Of these, methyl, tert-butyl, and cyclohexyl are preferable.

As the aryl group of $R^1$ to $R^4$, an aryl group having 6 to 30 carbon atoms is preferable. The aryl group may have a substituent. As the substituent, an alkyl group having 1 to 10 carbon atoms (for example, a methyl group, ethyl group, n-propyl group, isopropyl group, n-butyl group, sec-butyl group and tert-butyl group), halogen atom (for example, fluorine atom and chlorine atom), fluoroalkyl group having 1 to 20 carbon atoms (for example, trifluoromethyl group, trifluoroethyl group and pentafluoromethyl group), cycloalkyl group (cyclopentyl group, cyclohexyl group and cycloheptyl group), electron-attracting group (cyano group and nitro group) and the like can be given. For example, a phenyl group, naphthyl group, tolyl group, fluorene group and the like, or substituents in which substituents such as fluorine and fluoroalkyl group bond to the above mentioned groups such as 4-fluorophenyl, 4-fluoromethyl-phenyl, and 4-cyano-phenyl can be given.

Of these, 4-fluorophenyl and 4-trifluoromethyl-phenyl are preferable.

As the heterocycle of $R^1$ to $R^4$, a heterocycle containing a nitrogen atom, oxygen atom or sulfur atom as a hetero atom (the number of hetero atoms is preferably 3 or less, preferably 1 or 2) is preferable, and a five-membered ring, six-membered ring or fused ring composed of a combination of a five-membered ring and/or six-membered ring is preferable. A heterocycle having 3 to 20 carbon atoms is preferable. Examples thereof include a thiophene ring, furan ring, pyridine ring, pyrimidine ring, imidazole ring, quinoline ring, and imidazopyridine ring. Of these, a pyridine ring is preferable. The heterocycles may have a substituent such as a methyl group and ethyl group.

As the halogen atom of $R^1$ to $R^4$, fluorine and chlorine are preferable.

As the fluoroalkyl group of $R^1$ to $R^4$, a fluoroalkyl group having 1 to 20 carbon atoms, for example, a trifluoromethyl group, pentafluoroethyl group, perfluorocyclohexyl group and perfluoroadamantyl group can be given. Of these, trifluoromethyl is preferable.

$R^1$ and $R^2$, and $R^3$ and $R^4$ may be bonded to each other to form a ring, respectively, like specific example (B-9) or (B-10) described later.

Of the compounds of formula (I), preferred is a compound of the following formula (IIa) or (IIb),

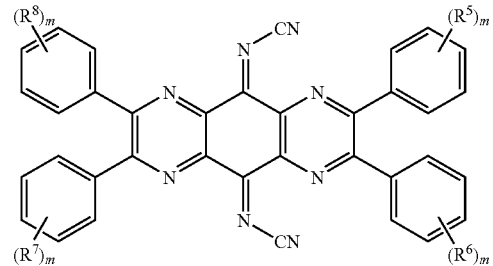

(IIa)

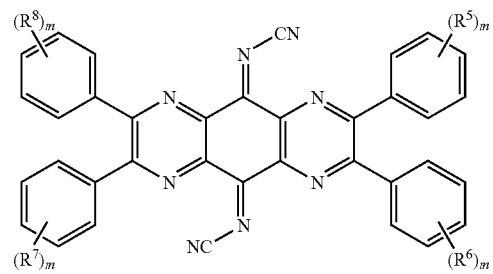

(IIb)

wherein $R^5$ to $R^8$ are independently hydrogen, an alkyl group, fluorine, a fluoroalkyl group or a cyano group; provided that at least one of $R^5$ to $R^8$ is fluorine or a fluoroalkyl group; and ms are independently an integer of 1 to 5.

Examples of the alkyl group and fluoroalkyl group of $R^5$ to $R^8$ are the same as those for $R^1$ to $R^4$ of the formula (I) as described above. When m is 2 or more, $R^5$s to $R^8$s independently may be the same or different.

The compounds of formula (II) are novel and have high stability such as heat resistance and sublimation properties, and high electron acceptability.

The reduction potential of an acetonitrile solution of the material for an organic EL device of the invention is preferably $-1.0V$ (vs $Fc^+/Fc$) or more and particularly preferably $-0.8V$ (vs $Fc^+/Fc$) or more. Fc represents ferrocene. The electron acceptability is enhanced by using a compound having a reduction potential of $-1.0V$ or more.

Specific examples of the material for an organic EL device of the invention are shown below. Although the following examples are examples of the compounds of formula (Ib) or (IIb), the isomers thereof (formula (Ia) or (IIa)) can be used.

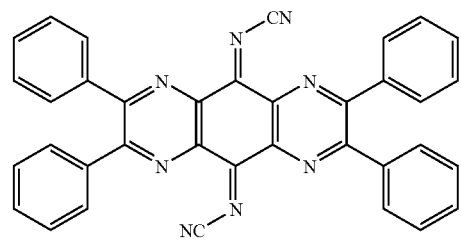

(A-1)

-continued
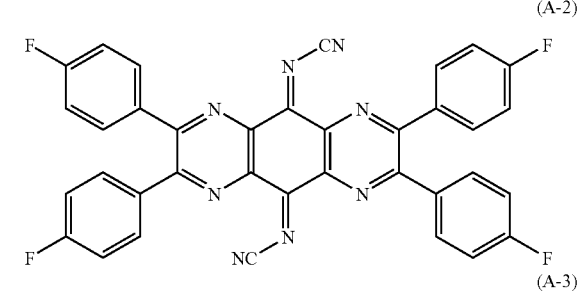
(A-2)
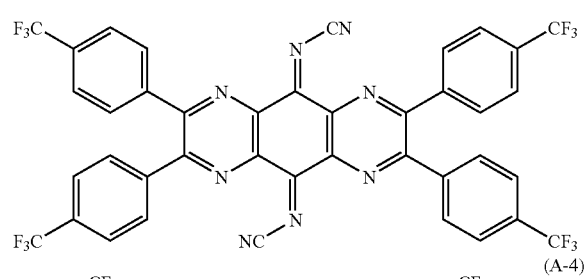
(A-3)
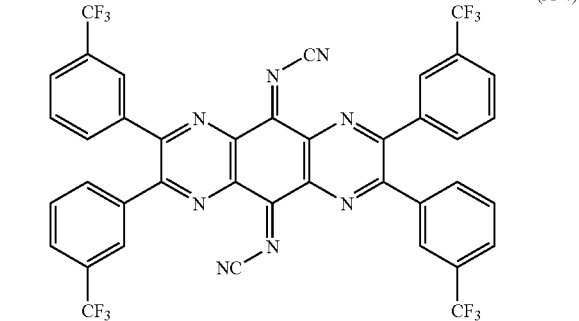
(A-4)
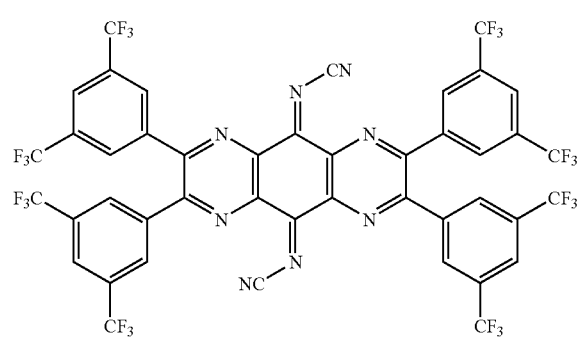
(A-5)
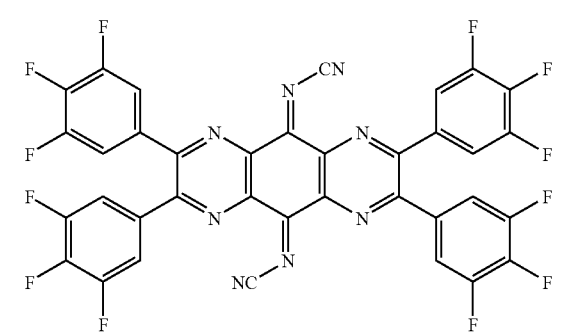
(A-6)
-continued
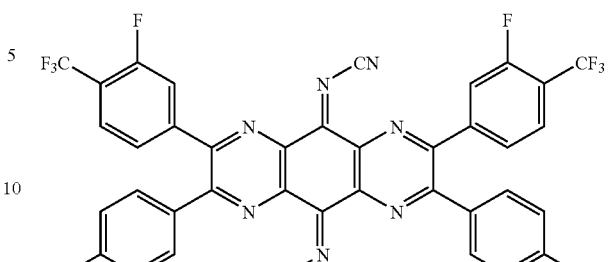
(A-7)
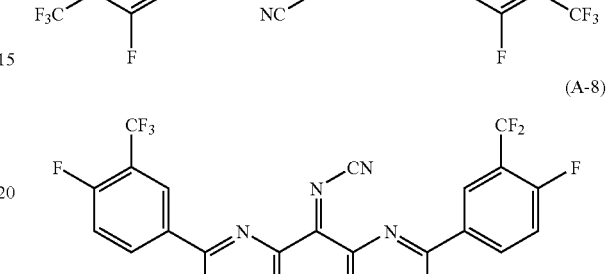
(A-8)
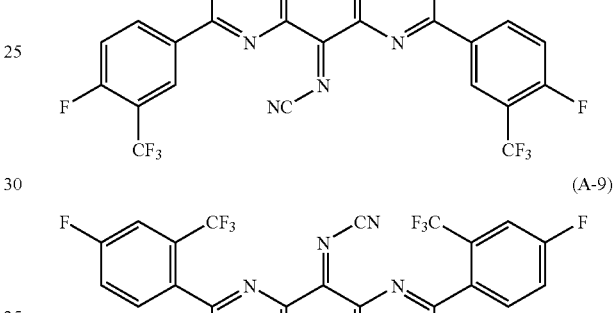
(A-9)
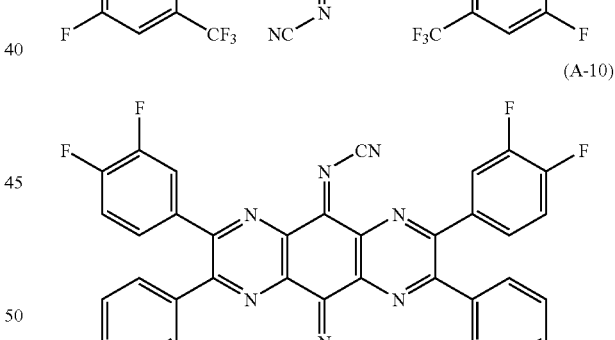
(A-10)
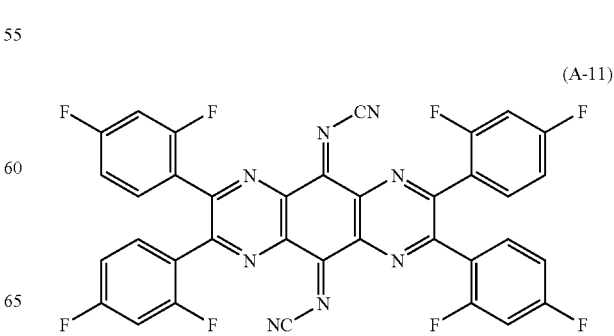
(A-11)

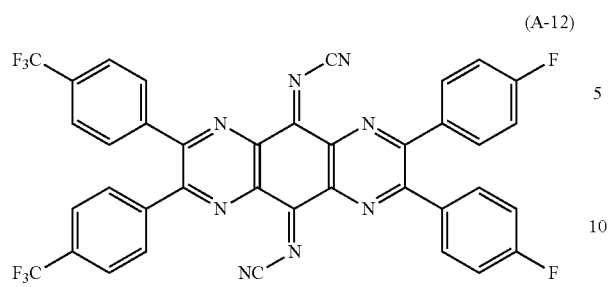
(A-12)
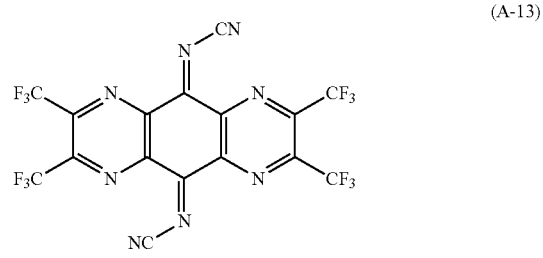
(A-13)
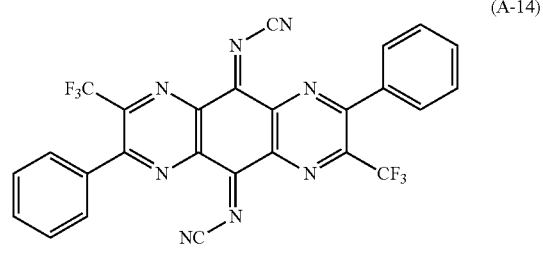
(A-14)
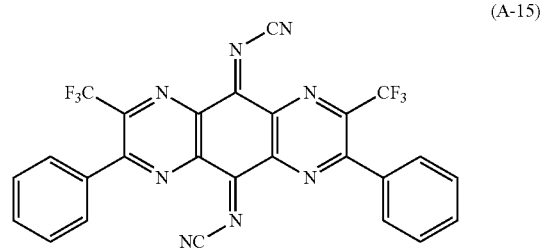
(A-15)
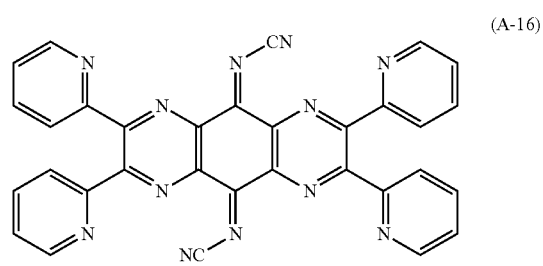
(A-16)
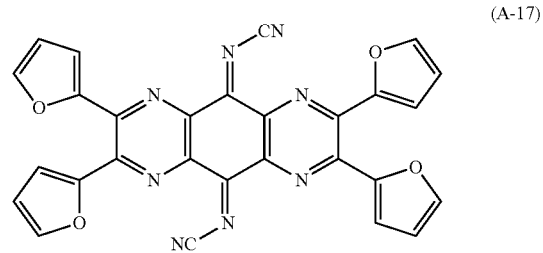
(A-17)
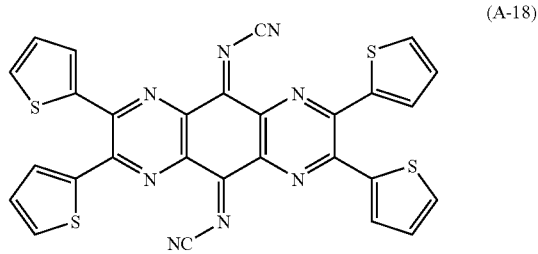
(A-18)
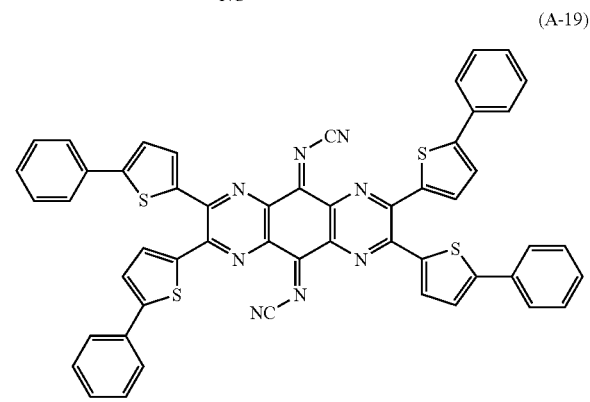
(A-19)
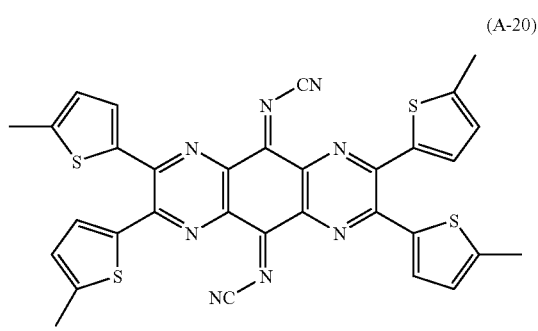
(A-20)
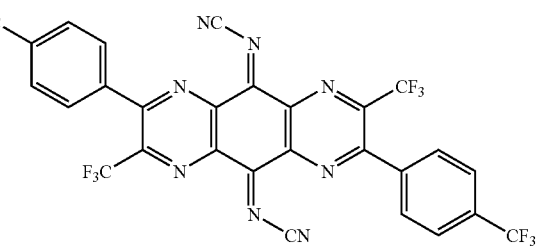
(A-21)
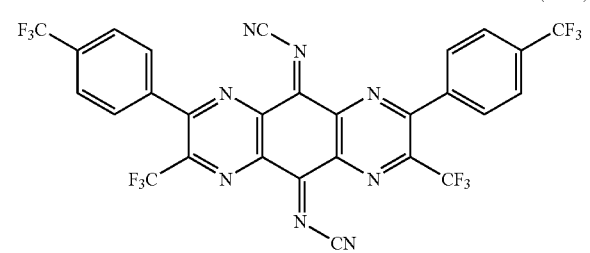
(A-22)

-continued
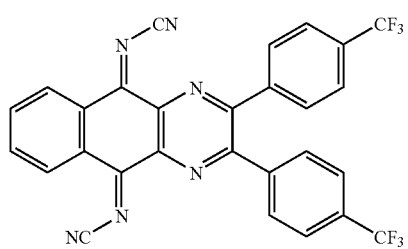
(B-1)
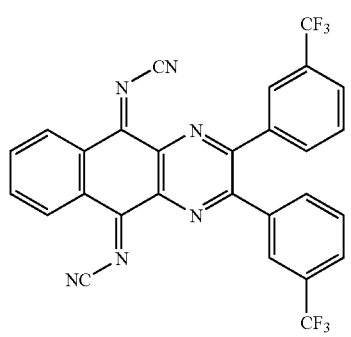
(B-2)
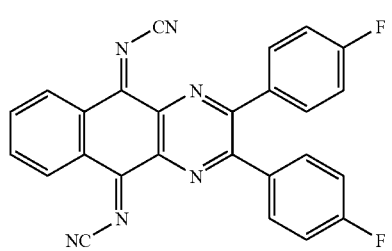
(B-3)
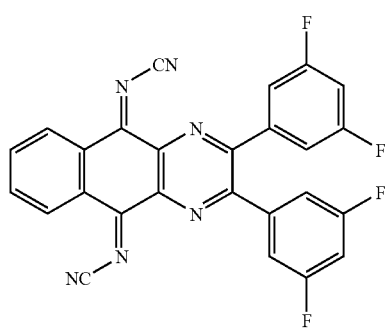
(B-4)
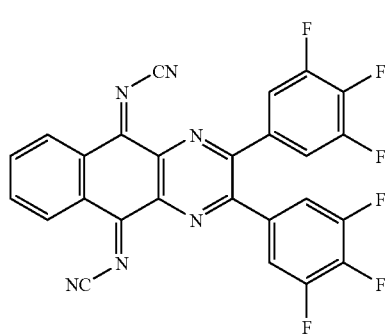
(B-5)
-continued
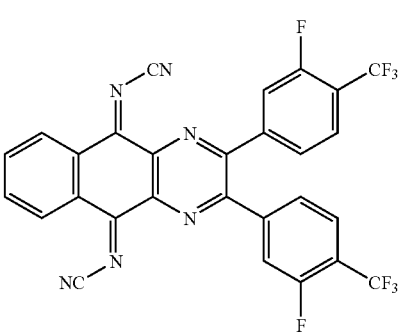
(B-6)
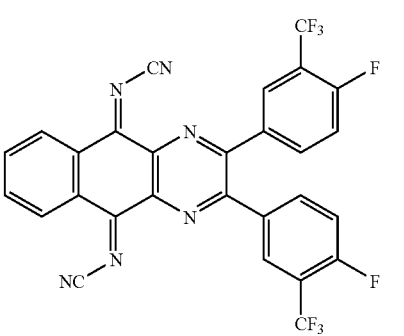
(B-7)
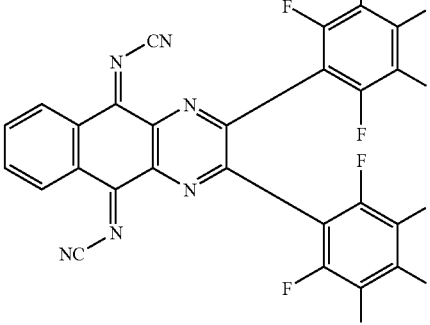
(B-8)
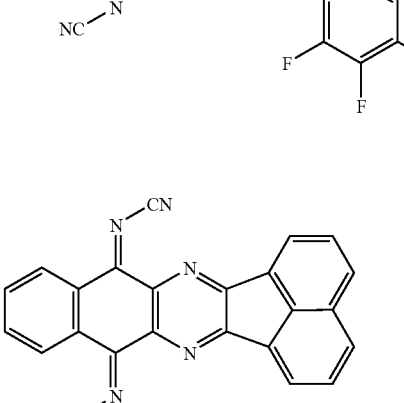
(B-9)
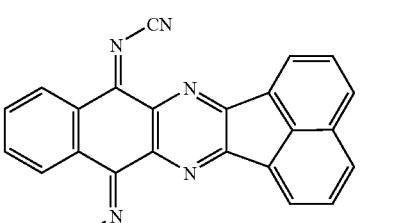
(B-10)

-continued (B-11)
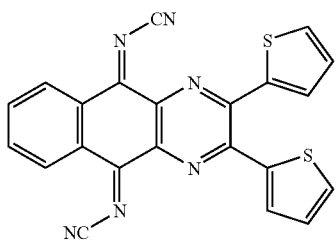

(B-12)
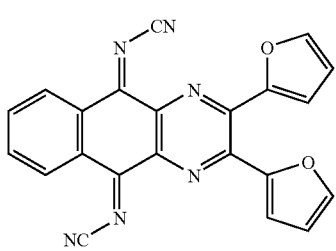

(B-13)
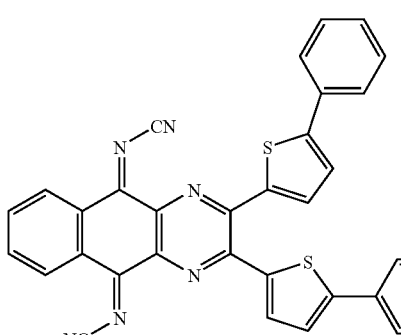

(B-14)
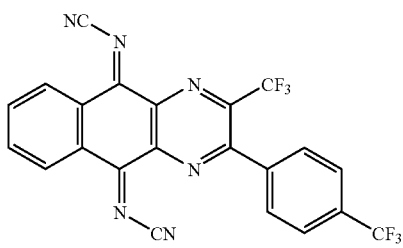

The imine derivative of the invention can be synthesized according to the following scheme 1, for example,

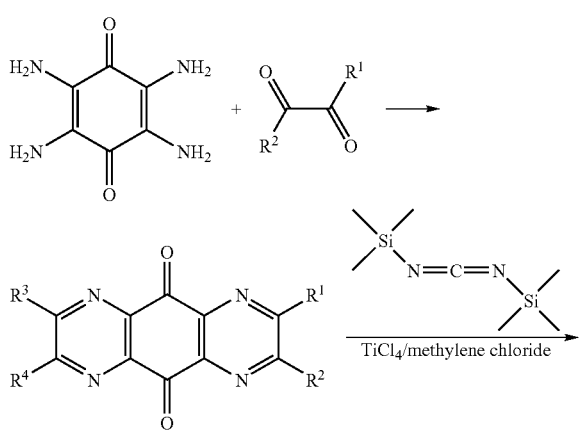

-continued

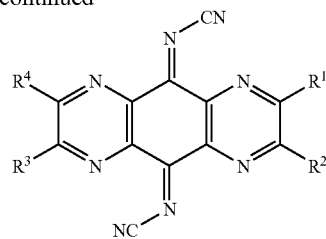

wherein $R^1$ to $R^4$ are the same as those of formula (I).

Specifically, tetraminodiphenoquinone synthesized according to the method described in Justus Liebigs Ann. Chem., 667, 55 to 71 (1963), and a benzyl derivative are reacted by heating at room temperature to 110° C. in a solvent selected from acetic acid, DMF, DMSO, an alcohol such as ethanol, and pyridine depending on the solubility or the like of raw materials to synthesize a dipyrazinobenzoquinone derivative.

The benzoquinone derivative is reacted with a compound for introducing an electron-attracting group such as bistrimethylsilylcarbodiimide. A method in which the reaction is performed in a solvent such as methylene chloride or carbon tetrachloride using titanium tetrachloride as a catalyst, a method in which the reaction is performed by heating in a solvent such as ethanol or pyridine can be used (JP-B-1957478).

The sublimation and purification of the crystal obtained by the above reactions can lower impurities. When such a purified material is used in an organic EL device, the device can have favorable performances such as long lifetime.

Next, the organic EL device of the invention will be described.

The organic EL device of the invention has an organic layer between a cathode and an anode. The organic layer is a thin-layer stack including a hole-injecting layer, a hole-transporting layer, an emitting layer and an electron-transporting layer in sequential order, and the hole-injecting layer contains the material for an organic EL device of the invention.

FIG. 1 is a schematic cross-sectional view showing one embodiment of the organic EL device of the invention.

In the organic EL device 1, an anode 10, hole-injecting layer 20, hole-transporting layer 30, emitting layer 40, electron-transporting layer 50, and cathode 60 are stacked on a substrate (not shown) in sequential order. In this device, the organic layer has a stack structure of the hole-injecting layer 20, hole-transporting layer 30, emitting layer 40, and electron-transporting layer 50. The hole-injecting layer 20 contains the material for an organic EL device of the invention. This structure can lower driving voltage and prolong lifetime of the organic EL device.

Layers other than the hole-injecting layer may contain the material for an organic EL device of the invention. In this case, the material may be used as a mixture with materials constituting the other layers described later. The organic layer may include an inorganic layer as a part thereof.

The content of the material for an organic EL device of the invention in the hole-injecting layer is preferably 1 to 100 mol %.

In the organic EL device of the invention, it is preferable that the hole-injecting layer contain a phenylenediamine compound of the following formula (III) in addition to the compound of formula (I),

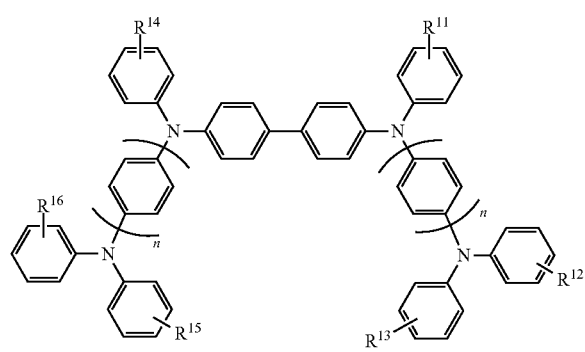

(III)

wherein $R^{11}$ to $R^{16}$ are independently hydrogen, a halogen atom, a trifluoromethyl group, an alkyl group, an aryl group or a heterocycle; $R^{11}$ to $R^{16}$ may form a naphthalene skeleton, a carbazole skeleton, or a fluorene skeleton with its bonding phenyl group; and n represents 1 or 2.

If a layer contains the phenylenediamine compound together, the uniformity, heat resistance, or carrier-injection properties thereof may be improved as compared with a layer which contains the material of the invention singly.

In the formula (III), fluorine is preferable as the halogen atom of $R^{11}$ to $R^{16}$.

As the alkyl group of $R^{11}$ to $R^{16}$, methyl, isopropyl, tert-butyl, and cyclohexyl are preferred, for example.

As the aryl group of $R^{11}$ to $R^{16}$, phenyl, naphthyl, and fluorenyl are preferable. These groups may be substituted with methyl or the like.

As the heterocycle of $R^{11}$ to $R^{16}$, pyridine and pyrazine are preferable, for example.

$R^{11}$ to $R^{16}$ may form a naphthalene skeleton, a carbazole skeleton, or a fluorene skeleton with its bonding phenyl group. These groups may be substituted with methyl or the like.

The content of the compound of the formula (III) in the hole-injecting layer is preferably 0.1 to 98 mol %.

Preferred examples of the compound (III) are given below.

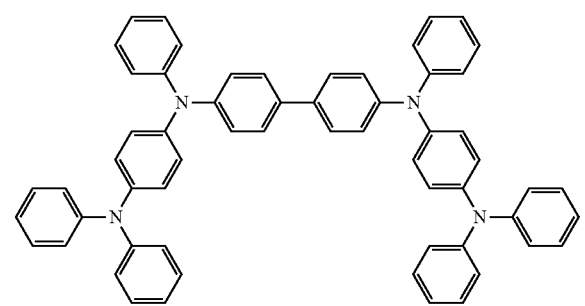

(C-1)

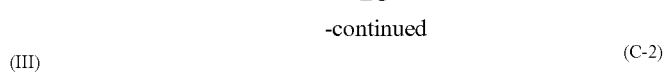

(C-2)

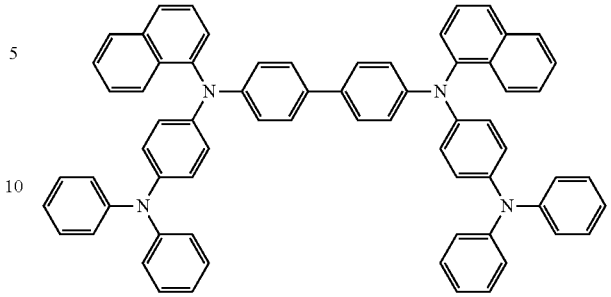

(C-3)

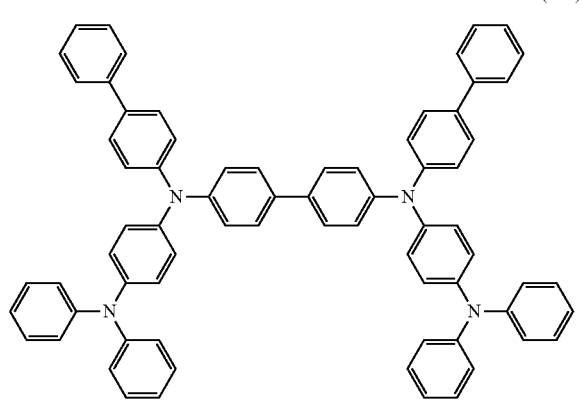

(C-4)

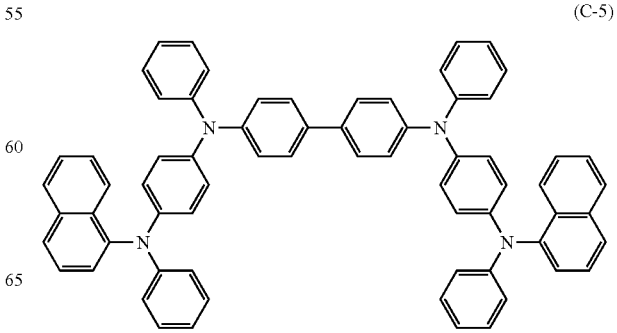

(C-5)

(C-6)
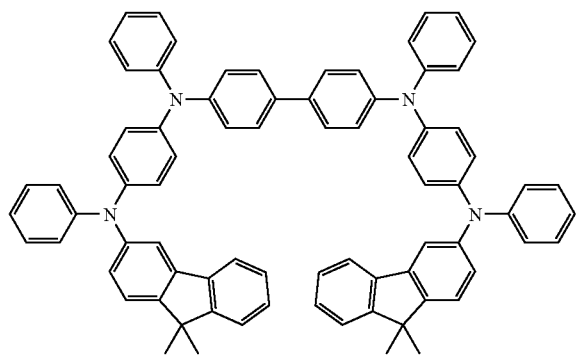

(C-7)

(C-8)
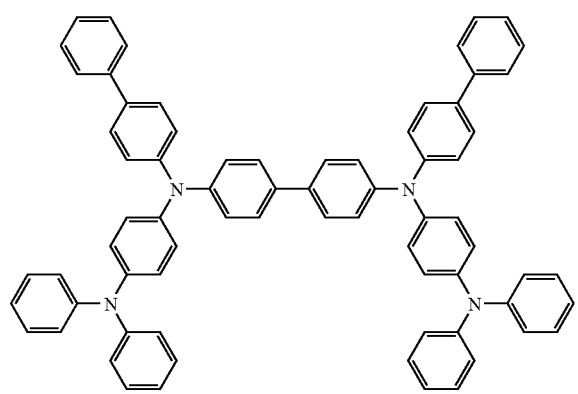

(C-9)
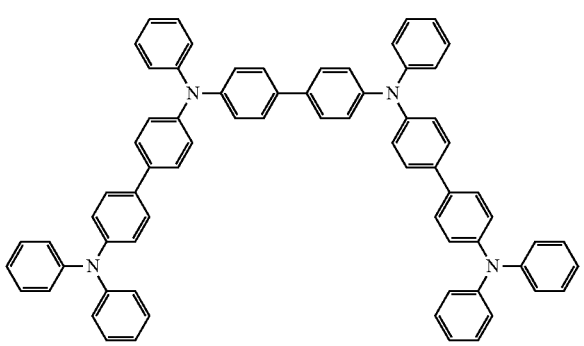

(C-10)
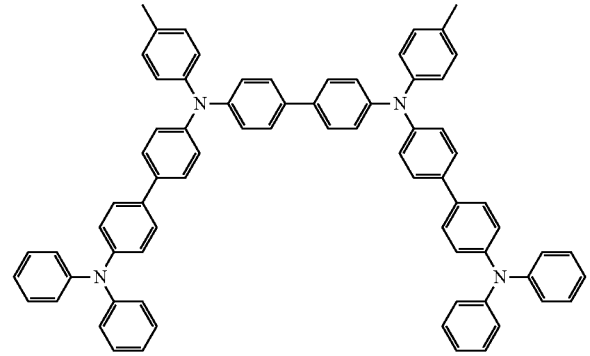

(C-11)

(C-12)
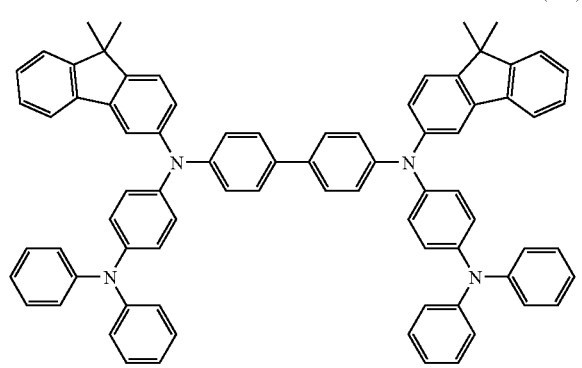

The material for an organic EL device of the invention may be used in devices which are of a structure other than the structure of the embodiment described above. For example, the material can be used as a material of each layer such as emitting layer forming the devices of the structures (1) to (15) shown below.

(1) Anode/emitting layer/cathode
(2) Anode/hole-transporting layer/emitting layer/cathode
(3) Anode/emitting layer/electron-transporting layer/cathode
(4) Anode/hole-transporting layer/emitting layer/electron-transporting layer/cathode
(5) Anode/hole-transporting layer/emitting layer/adhesion-improving layer/cathode
(6) Anode/hole-injecting layer/hole-transporting layer/emitting layer/electron-transporting layer/cathode (FIG. 1)
(7) Anode/hole-transporting layer/emitting layer/electron-transporting layer/electron-injecting layer/cathode
(8) Anode/hole-injecting layer/hole-transporting layer/emitting layer/electron-transporting layer/electron-injecting layer/cathode
(9) Anode/insulating layer/hole-transporting layer/emitting layer/electron-transporting layer/cathode

(10) Anode/hole-transporting layer/emitting layer/electron-transporting layer/insulating layer/cathode

(11) Anode/inorganic semiconductor layer/insulating layer/hole-transporting layer/emitting layer/insulating layer/cathode

(12) Anode/insulating layer/hole-transporting layer/emitting layer/electron-transporting layer/insulating layer/cathode

(13) Anode/hole-injecting layer/hole-transporting layer/emitting layer/electron-transporting layer/insulating layer/cathode

(14) Anode/insulating layer/hole-injecting layer/hole-transporting layer/emitting layer/electron-transporting layer/electron-injecting layer/cathode

(15) Anode/insulating layer/hole-injecting layer/hole-transporting layer/emitting layer/electron-transporting layer/electron-injecting layer/insulating layer/cathode Among these, usually, the structures (4), (6), (7), (8), (12), (13) and (15) are preferably used.

Each member constituting the organic EL device of the invention will be described below.

(Substrate)

The substrate is a supporting body in which organic EL devices are arranged and formed on a main surface of the substrate. The transparent substrate is preferably a flat and smooth substrate having a 400-to-700-nm-visible-light transmittance of 50% or more when light is outcoupled through the supporting substrate. Transparency is not required when the supporting substrate is positioned in the direction opposite to the light-outcoupling direction.

Known substrates may be used. Examples of the substrate include quartz, glass, metal foil, and resin film or sheet. Of these, quartz or glass is preferable.

Examples of the glass plate include soda-lime glass, barium/strontium-containing glass, lead glass, aluminosilicate glass, borosilicate glass, barium borosilicate glass, and quartz. Examples of the polymer plate include methacryl resins represented by polymethylmethacrylate (PMMA), polyesters such as polyethylene naphthalate (PEN) and polybutylene naphthalate (PBN), polycarbonate, polyethersulfide, and polysulfone.

The substrate may be a stack or surface-finished to have a low water permeability or gas permeability.

(Anode)

An anode having a great work function relative to the vacuum level of an electrode material may be used to inject holes efficiently. For example, metals such as aluminum (Al), chromium (Cr), molybdenum (Mo), tungsten (W), copper (Cu), silver (Ag) and gold (Au) and alloys thereof; oxides and the like thereof; alloys of tin oxide ($SnO_2$) and antimony (Sb); ITO (Indium tin oxide); InZnO (Indium Zinc oxide); alloys of zinc oxide (ZnO) and aluminum; and oxides and the like of these metals and alloys can be used singly or in mixture thereof. When transparency is required for the anode, indium tin oxide alloy (ITO), tin oxide (NESA), indium zinc oxide alloy (IZO), gold, silver, platinum, copper, and the like may be used. When the anode is used as a reflective electrode which does not require transparency, metals and alloys such as aluminum, molybdenum, chromium, and nickel as well as the metals may also be used.

In particular, even if an anode having a low work function (for example, 5.0 eV or less) is used with a hole-injecting layer containing the material for an organic EL device of the invention, transferring and receiving electrons is possible, and satisfactory injection is performed.

The anode can be formed by forming these electrode materials into a thin film by vapor deposition, sputtering or the like.

In the case where emission from the emitting layer is taken out through the anode, the transmittance of the anode to the emission is preferably more than 10%. The sheet resistance of the anode is preferably several hundred Ω/□ or less. The film thickness of the anode, which varies depending upon the material thereof, is usually from 10 nm to 1 μm, preferably from 10 to 200 nm.

When fabricating an organic EL device of top-emission type, an anode may be a stack of a first layer which excels in light reflectivity, and a second layer arranged on the first layer which transmits light and has a great work function.

For example, the first layer is formed of aluminum or an alloy containing aluminum as the main component. The accessary component of the alloy may be one containing at least one element having a lower work function than aluminum of the main component. As the accessary component, lanthanoid elements are preferable. Although the work function of the lanthanoid elements is not great, by containing these elements, the stability of the anode is improved with the satisfactory hole injecting property of the anode. The first layer may contain silicon (Si), copper (Cu) or the like as the accessary component as well as the lanthanoid elements.

The total content of accessary components in the aluminum alloy layer constituting the first layer is preferably about 10 wt % or less when Nd, Ni or Ti which stabilizes aluminum is used. This enables to keep the aluminum alloy layer stable in the production process of an organic EL device, and to obtain processing accuracy and chemical stability while maintaining the refractivity of the aluminum alloy layer. Further, the anode can be improved in conductivity and adhesion to the substrate.

As an example of the second layer, a layer formed of at least one of an aluminum alloy oxide, molybdenum oxide, zirconium oxide, chromium oxide and tantalum oxide can be given. Nitrides of these metals may be used. When the second layer is an oxide layer (including a natural oxide film) of an aluminum alloy containing a lanthanoid element as an accessary component, the second layer containing the lanthanoid element has a good transmittance due to the high transmittance of the oxide of the lanthanoid element. As a result, it is possible to maintain a high reflectance on the surface of the first layer. The second layer may be a transparent conductive layer such as ITO or IZO. These conductive layer can improve the electron-injecting properties of an anode.

In order to enhance adhesion between an anode and a substrate, a conductive layer may be arranged on the surface on which the anode contacts the substrate. As the conductive layer, a transparent conductive layer such as ITO or IZO can be given.

If a display formed of this organic EL device is driven in the active matrix manner, the anode is patterned in each pixel and arranged so as to connect to a thin film transistor for driving arranged on the substrate. Furthermore, an insulating layer is provided on the anode such that a surface of the anode of each pixel is exposed through an opening of this insulating layer.

(Emitting Layer)

The emitting layer of the organic EL device has the following functions (1), (2) and (3) in combination.

(1) Injection function: function of allowing injection of holes from the anode or hole-injecting layer and injection of electrons from the cathode or electron-injecting layer upon application of an electric field (2) Transporting function: function of moving injected carriers (electrons and holes) due to the force of an electric field (3) Emitting function: function of allowing electrons and holes to recombine to emit light Note that electrons and holes may be injected into the emitting layer with different degrees, or the transportation capabilities indicated by the mobility of holes and electrons may differ. It is preferable that the emitting layer move either electrons or holes.

As the method of forming the emitting layer, a known method such as deposition, spin coating, or an LB method may be applied. It is preferable that the emitting layer be a molecular deposition film. The molecular deposition film is a thin film formed by depositing a material compound in a vapor phase or by solidifying a material compound in a solution or liquid state. The molecular deposition film is distinguished from a thin film (molecular accumulation film) formed using the LB method by the difference in aggregation structure or higher order structure, or the difference in function due to the difference in structure.

The emitting layer may also be formed by dissolving a binder such as a resin and a material compound in a solvent to obtain a solution, and forming a thin film from the solution by spin coating or the like, as disclosed in JP-A-57-51781.

In the invention, if need arises, known emitting materials other than the emitting materials formed of the novel compound of the invention may be contained in the emitting layer insofar as the object of the invention is not impaired. An emitting layer containing other known emitting materials may be stacked on the emitting layer containing the emitting materials formed of the novel compound of the invention.

As the emitting material or the doping material used for the emitting layer, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, a quinoline metal complex, an aminoquinoline metal complex, a benzoquinoline metal complex, imine, diphenyl ethylene, vinylanthracene, diaminocarbazol, pyran, thiopyran, polymethine, merocyanine, an imidazole chelate oxanoid compound, quinacridone, rubrene, a fluorescent pigment and like can be given. Note that the emitting material and the doping material are not limited to these compounds.

Among these, preferred dopant materials are following (D-1) to (D-73).

N,N,N',N',7,14-hexaphenylacenaphtho[1,2-k]fluoranthene-3,10-diamine (D-1)
N,N',7,14-tetraphenyl-N,N-di-p-tolylacenaphtho[1,2-k]fluoranthene-3,10-diamine (D-2)
N,N'-bis(4-methoxyphenyl)-N,N',7,14-tetraphenylacenaphtho[1,2-k]fluoranthene-3,11-diamine (D-4)
N,N,N',N'-tetrakis(4-ethylphenyl)-7,14-diphenylacenaphtho[1,2-k]fluoranthene-3,11-diamine (D-5)
N,N,N',N'-tetrakis(4-methoxy-3,5-dimethylphenyl)-7,14-diphenylacenaphtho[1,2-k]fluoranthene-3,10-diamine (D-6)
(E)-N,N'-(4,4'-(ethene-1,2-diyl)bis(4,1-phenylene))bis(N-(biphenyl-4-yl)biphenyl-4-amine) (D-7)
(E)-N,N'-(4,4'-(ethene-1,2-diyl)bis(4,1-phenylene))bis(N-phenylnaphthalene-2-amine) (D-8)
(E)-N,N'-(4,4'-(ethene-1,2-diyl)bis(4,1-phenylene))bis(N-phenylphenanthrene-9-amine) (D-9)
(E)-N,N'-(4,4'-(1,2-diphenylethene-1,2-diyl)bis(4,1-phenylene))bis(N-phenylnaphthalene-2-amine) (D-10)
N,N'-bis(4-methoxyphenyl)-N,N'-diphenyl-1,1'-binaphthyl-4,4'-diamine (D-11)
N,N,N',N'-tetra-p-tolylnaphthalene-1,4-diamine (D-12)
N,N'-di(naphthalene-2-yl)-N,N'-diphenylnaphthalene-2,6-diamine (D-13)
N,N-bis(4-methoxyphenyl)-N,N'-diphenyl-1,1'-binaphthyl-4,4'-diamine (D-14)
4,4'-(naphthalene-1,4-diyl)bis(N,N-diphenylaniline) (D-15)
N,N'-(3,3'-(anthracene-9,10-diyl)bis(3,1-phenylene))bis(N-phenylnaphthalene-1-amine) (D-16)
N,N',2,6-tetraphenyl-N,N'-di-m-tolylanthracene-9,10-diamine (D-17)
N,N,N',N'-tetra-p-tolyl-9,9'-bianthracene-10,10'-diamine (D-18)
N,N-diphenylpyrene-1-amine (D-19)
N,N-diethyl-N'-phenyl-N'-(pyrene-1-yl)benzene-1,4-diamine (D-20)
N-(naphthalene-2-yl)-N-phenylfluoranthene-3-amine (D-21)
N,N-di-p-tolylphenanthrene-9-amine (D-22)
N,N,10-triphenylanthracene-9-amine (D-23)
N,N,N',N'-tetraphenylperylene-3,9-diamine (D-24)
N,N-di(biphenyl-3-yl)-N,N'-diphenylperylene-3,9-diamine (D-25)
N,N,N',N'-tetraphenylchrysene-6,12-diamine (D-26)
N,N,N',N'-tetra-p-tolylchrysene-6,12-diamine (D-27)
N,N,N',N'-tetra-m-tolylchrysene-6,12-diamine (D-28)
N,N,N',N'-tetrakis(3,4-dimethylphenyl)chrysene-6,12-diamine (D-29)
N,N,N',N'-tetrakis(3,5-dimethylphenyl)chrysene-6,12-diamine (D-30)
N,N,N',N'-tetrakis(2,4-dimethylphenyl)chrysene-6,12-diamine (D-31)
N,N,N',N'-tetrakis(2,3,4,5-tetramethylphenyl)chrysene-6,12-diamine (D-32)
N,N'-bis(3,4-dimethylphenyl)-N,N'-di-p-tolylchrysene-6,12-diamine (D-33)
N,N'-bis(4-ethylphenyl)-N,N'-diphenylchrysene-6,12-diamine (D-34)
N,N'-bis(4-isopropylphenyl)-N,N'-diphenylchrysene-6,12-diamine (D-35)
N,N'-bis(4-t-butylphenyl)-N,N'-diphenylchrysene-6,12-diamine (D-36)
N,N,N',N'-tetra(naphthalene-2-yl)chrysene-6,12-diamine (D-37)
6,12-bis(3,6-dimethyl-9H-carbazole-9-yl)chrysene (D-38)
N,N,N',N'-tetrakis(3-t-butyl-5-methylphenyl)chrysene-6,12-diamine (D-39)
N,N,N',N'-tetrakis(3,5-di-t-butylphenyl)chrysene-6,12-diamine (D-40)
N,N'-bis(3,5-di-t-butylphenyl)-N,N'-bis(3,4,5-trimethylphenyl)chrysene-6,12-diamine (D-41)
N,N'-bis(3,5-di-t-butylphenyl)-N,N'-bis(3,4-dimethylphenyl)chrysene-6,12-diamine (D-42)
N,N'-bis(3,5-di-t-butylphenyl)-N,N'-bis(3,5-dimethylphenyl)chrysene-6,12-diamine (D-43)
N,N'-bis(3-t-butyl-5-methylphenyl)-N,N-bis(3,5-dimethylphenyl)chrysene-6,12-diamine (D-44)
N,N'-bis(3-t-butyl-5-methylphenyl)-N,N-bis(3-isopropyl-5-methylphenyl)chrysene-6,12-diamine (D-45)
N,N,N',N'-tetrakis(3-t-butyl-5-isopropylphenyl)chrysene-6,12-diamine (D-46)
N,N-bis(3,5-di-t-butylphenyl)-N,N-bis(3,5-diethyl-4-methylphenyl)chrysene-6,12-diamine (D-47)
N,N'-bis(3,5-di-t-butylphenyl)-N,N'-bis(4-ethyl-3-methylphenyl)chrysene-6,12-diamine (D-48)
N,N'-bis(3,5-di-t-butylphenyl)-N,N'-bis(3-isopropyl-5-methylphenyl)chrysene-6,12-diamine (D-49)
N-(3-t-butyl-5-methylphenyl)-N,N-bis(3,5-dimethylphenyl)-N'-(3-isopropyl-5-methylphenyl)chrysene-6,12-diamine (D-50)

N,N'-bis(3,4-dimethylphenyl)-N,N'-bis(4-isopropyl-3,5-dimethylphenyl)chrysene-6,12-diamine (D-51)

N,N,N',N'-tetrakis(3,5-diisopropylphenyl)chrysene-6,12-diamine (D-52)

N,N-bis(3,5-diisopropylphenyl)-N,N'-bis(3,4-dimethylphenyl)chrysene-6,12-diamine (D-53)

N,N'-bis(3,5-dimethylphenyl)-N,N'-bis(3-isopropyl-5-methylphenyl)chrysene-6,12-diamine (D-54)

N,N-bis(3,5-diisopropylphenyl)-N,N-bis(3,5-dimethylphenyl)chrysene-6,12-diamine (D-55)

N,N'-bis(3,4-dimethylphenyl)-N,N'-bis(3,4,5-trimethylphenyl)chrysene-6,12-diamine (D-56)

N,N'-bis(3,5-dimethylphenyl)-N,N'-bis(3,4,5-trimethylphenyl)chrysene-6,12-diamine (D-57)

N,N,N',N'-tetrakis(3,4,5-trimethylphenyl)chrysene-6,12-diamine (D-58)

N,N,N',N'-tetramesitylchrysene-6,12-diamine (D-59)

N,N'-diphenyl-N,N'-di-p-tolylchrysene-6,12-diamine (D-60)

N,N'-di(naphthalene-2-yl)-N,N'-diphenylchrysene-6,12-diamine (D-61)

N,N'-di(biphenyl-3-yl)-N,N'-diphenylchrysene-6,12-diamine (D-62)

N,N'-bis(9,9-dimethyl-9H-fluorene-3-yl)-N,N'-bis(3,4,5-trimethylphenyl)chrysene-6,12-diamine (D-63)

N,N'-bis(9,9-dimethyl-9H-fluorene-3-yl)-N,N'-bis(3,4-dimethylphenyl)chrysene-6,12-diamine (D-64)

N,N,N',N'-tetrakis(9,9-dimethyl-9H-fluorene-3-yl)chrysene-6,12-diamine (D-65)

N,N,N',N'-tetrakis(3,5-dicyclohexylphenyl)chrysene-6,12-diamine (D-66)

N,N'-bis(3,5-dimethylphenyl)-N,N'-bis(3-(1,1-diphenylethyl)-5-methylphenyl)chrysene-6,12-diamine (D-67)

N,N'-bis(3,5-bis(2-phenylpropane-2-yl)phenyl)-N,N'-bis(3,5-dimethylphenyl)chrysene-6,12-diamine (D-68)

N,N,N',N'-tetrakis(5,6,7,8-tetrahydronaphthalene-2-yl)chrysene-6,12-diamine (D-69)

N,N,N',N'-tetrakis(5,6,7,8-tetrahydronaphthalene-1-yl)chrysene-6,12-diamine (D-70)

N,N'-bis(2,3-dimethylphenyl)-N,N'-bis(3-methyl-5,6,7,8-tetrahydronaphthalene-1-yl)chrysene-6,12-diamine (D-71)

N,N'-bis(3,4-dimethylphenyl)-N,N'-di(naphthalene-2-yl)chrysene-6,12-diamine (D-72)

N,N'-bis(3,5-di-t-butylphenyl)-N,N'-di(naphthalene-2-yl)chrysene-6,12-diamine (D-73)

As the host material for use in the emitting layer, the compounds of the following formulas (i) to (ix) are preferred.

Asymmetrical anthracene of the following formula (i)

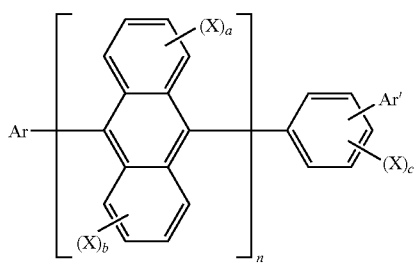

wherein Ar is a substituted or unsubstituted condensed aromatic group having 10 to 50 carbon atoms that form a ring, Ar' is a substituted or unsubstituted aromatic group having 6 to 50 ring carbon atoms, X is a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group or a hydroxyl group.

a, b and c are independently an integer of 0 to 4.

n is an integer of 1 to 3. When n is two or more, the groups in [ ] may be the same or different.

Asymmetrical monoanthracene derivatives of the following formula (ii)

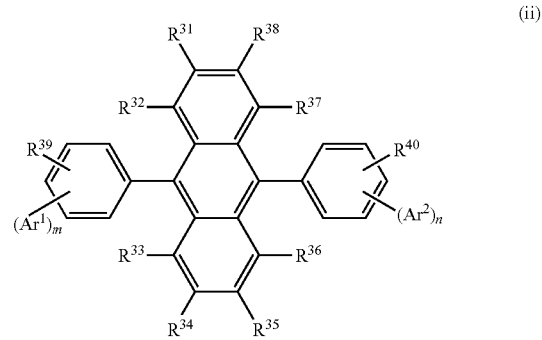

wherein $Ar^1$ and $Ar^2$ are independently a substituted or unsubstituted aromatic ring group having 6 to 50 ring carbon atoms, and m and n are independently an integer of 1 to 4, provided that in the case where m=n=1 and $Ar^1$ and $Ar^2$ are symmetrically bonded to the benzene rings, $Ar^1$ and $Ar^2$ are not the same, and in the case where m or n is an integer of 2 to 4, m is different from n.

$R^{31}$ to $R^{40}$ are independently a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group.

Asymmetrical pyrene derivatives of the following formula (iii)

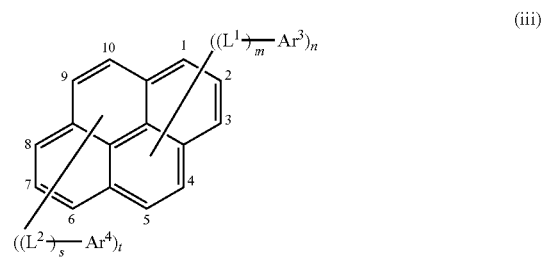

wherein $Ar^3$ and $Ar^4$ are independently a substituted or unsubstituted aromatic group having 6 to 50 ring carbon atoms;

$L^1$ and $L^2$ are independently a substituted or unsubstituted phenylene group, a substituted or unsubstituted naphthalenylene group, a substituted or unsubstituted fluorenylene group, or a substituted or unsubstituted dibenzosilolylene group;

m is an integer of 0 to 2, n is an integer of 1 to 4, s is an integer of 0 to 2, and t is an integer of 0 to 4;

$L^1$ or $Ar^3$ bonds at any one position of 1 to 5 of the pyrene, and $L^2$ or $Ar^4$ bonds at any one position of 6 to 10 of the pyrene;

provided that when n+t is an even number, $Ar^3$, $Ar^4$, $L^1$ and $L^2$ satisfy the following (1) and (2):

(1) $Ar^3 \neq Ar^4$ and/or $L^1 \neq L^2$ where $\neq$ means these substituents are groups having different structures from each other, (2) when $Ar^3 = Ar^4$ and $L^1 = L^2$,
  (2-1) m≠s and/or n≠t, or
  (2-2) when m=s and n=t,
    when (2-2-1) $L^1$ and $L^2$, or the pyrene each bond to $Ar^3$ and $Ar^4$ at different positions, or
    (2-2-2) $L^1$ and $L^2$, or the pyrene bond to $Ar^3$ and $Ar^4$ at the same positions,
  the pyrene is neither substituted by $L^1$ and $L^2$, or $Ar^3$ and $Ar^4$ at 1 and 6 positions, nor 2 and 7 positions.

Asymmetrical anthracene derivatives of the following formula (iv)

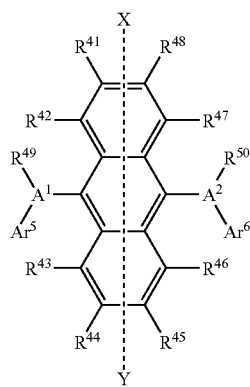

(iv)

wherein $A^1$ and $A^2$ are independently a substituted or unsubstituted condensed aromatic ring group having 10 to 20 ring carbon atoms, $Ar^5$ and $Ar^6$ are independently a hydrogen atom or a substituted or unsubstituted aromatic ring group with 6 to 50 ring carbon atoms, $R^{41}$ to $R^{50}$ are independently a hydrogen atom or a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group, and each of $Ar^5$, $Ar^6$, $R^{49}$ and $R^{50}$ may be plural, and adjacent groups thereof may form a saturated or unsaturated ring structure, provided that groups do not symmetrically bond to 9 and 10 positions of the central anthracene with respect to X-Y axis.)

Anthracene derivative of the following formula (v)

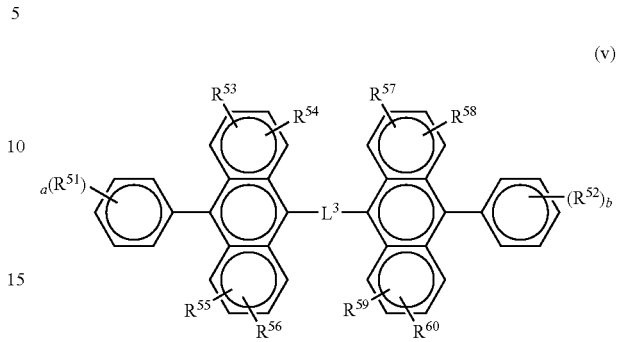

(v)

wherein $R^{51}$ to $R^{60}$ are independently a hydrogen atom, an alkyl group, a cycloalkyl group, an aryl group which may be substituted, an alkoxy group, an aryloxy group, an alkylamino group, an alkenyl group, an arylamino group or a heterocyclic group which may be substituted; a and b are independently an integer of 1 to 5; when they are 2 or more, $R^{51}$s or $R^{52}$s may be the same or different, or $R^{51}$s or $R^{52}$s may be bonded together to form a ring; $R^{53}$ and $R^{54}$, $R^{55}$ and $R^{56}$, $R^{57}$ and $R^{58}$, or $R^{59}$ and $R^{60}$ may be bonded together to form a ring; and $L^3$ is a single bond, —O—, —S—, —N(R)— (R is an alkyl group or a substituted or unsubstituted aryl group), an alkylene group or an arylene group.

Anthracene derivatives of the following formula (vi)

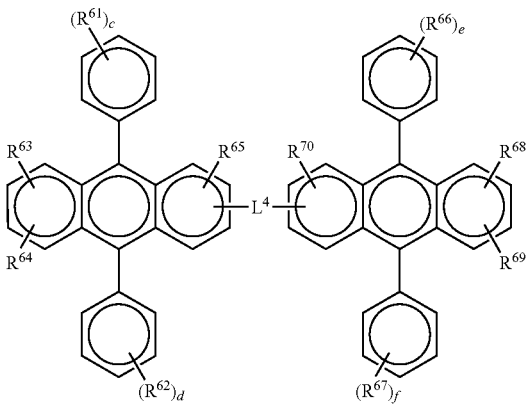

(vi)

wherein $R^{61}$ to $R^{70}$ are independently a hydrogen atom, an alkyl group, a cycloalkyl group, an aryl group, an alkoxy group, an aryloxy group, an alkylamino group, an arylamino group or a heterocyclic group which may be substituted; c, d, e and f are independently an integer of 1 to 5; when they are 2 or more, $R^{61}$s, $R^{62}$s, $R^{66}$s or $R^{67}$s may be the same or different, $R^{61}$s, $R^{62}$s, $R^{66}$s or $R^{67}$s may be bonded together to form a ring, or $R^{63}$ and $R^{64}$, or $R^{68}$ and $R^{69}$ may be bonded together to form a ring; and $L^4$ is a single bond, —O—, —S—, —N(R)— (R is an alkyl group or a substituted or unsubstituted aryl group), an alkylene group or an arylene group.

Spirofluorene derivatives of the following formula (vii)

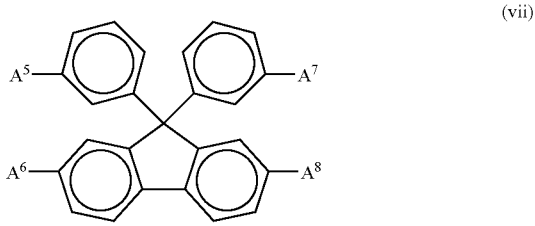

(vii)

wherein $A^5$ to $A^8$ are independently a substituted or unsubstituted biphenyl group or a substituted or unsubstituted naphthyl group.

Condensed ring-containing compounds of the following formula (viii)

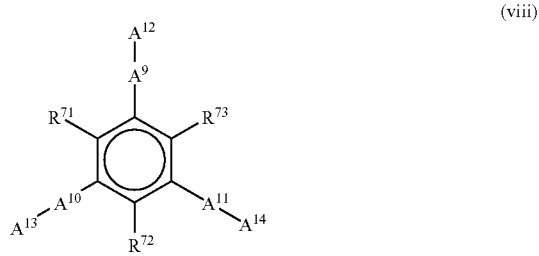

(viii)

wherein $A^9$ to $A^{14}$ are the same as the above-described ones and $R^{71}$ to $R^{73}$ are independently a hydrogen atom, alkyl group having 1 to 6 carbon atoms, cycloalkyl group having 3 to 6 carbon atoms, alkoxy group having 1 to 6 carbon atoms, aryloxy group having 5 to 18 carbon atoms, aralkyloxy group having 7 to 18 carbon atoms, arylamino group having 5 to 16 carbon atoms, nitro group, cyano group, ester group having 1 to 6 carbon atoms, or a halogen atom, provided that at least one of $A^9$ to $A^{14}$ is a group having a condensed aromatic ring with three or more rings.

Fluorene compounds of the following formula (ix)

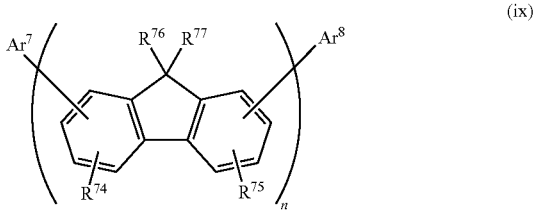

(ix)

wherein $R^{74}$ and $R^{75}$ are a hydrogen atom, a substituted or unsubstituted alkyl group, substituted or unsubstituted aralkyl group, substituted or unsubstituted aryl group, substituted or unsubstituted heterocyclic group, substituted amino group, cyano group, or a halogen atom. $R^{74}$s or $R^{74}$s bonded to different fluorene groups may be the same or different, and $R^{74}$ and $R^{75}$ bonded to the same fluorene group may be the same or different. $R^{76}$ and $R^{77}$ are a hydrogen atom, a substituted or unsubstituted alkyl group, substituted or unsubstituted aralkyl group, substituted or unsubstituted aryl group, or substituted or unsubstituted heterocyclic group, provided that $R^{76}$s or $R^{77}$s bonded to different fluorene groups may be the same or different, and $R^{76}$ and $R^{77}$ bonded to the same fluorene group may be the same or different. $Ar^7$ and $Ar^8$ are a substituted or unsubstituted condensed polycyclic aromatic group with the total number of benzene rings of three or more, or a substituted or unsubstituted condensed polycyclic heterocyclic group which is bonded to a fluorene group at a carbon atom with the total number of benzene rings and heterocyclic rings of three or more, provided that $Ar^7$ and $Ar^8$ may be the same or different. n is an integer of 1 to 10.

Among the above compounds, the host material is preferably the anthracene derivative, more preferably the monoanthracene derivative, and particularly preferably the asymmetrical anthracene.

Phosphorescent compounds can be used as an emitting material. When using a phosphorescent compound, compounds containing a carbazole ring are preferred for a host material. A dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable.

The compounds containing a carbazole ring, which are a host suitable for phosphorescence emission, is a compound which causes a phosphorescent compound to emit light as a result of energy transfer from its excited state to the phosphorescent compound. The host compound is not limited so long as the compound can transfer its excited energy to a phosphorescent compound and it can be selected according to purposes. The host compound may contain any heterocyclic ring other than a carbazole ring.

Specific examples of the host compounds include carbazole derivatives, triazole derivatives, oxazole derivatives, oxadiazole derivatives, imidazole derivatives, polyarylalkane derivatives, pyrazoline derivatives, pyrazolone derivatives, phenylanediamine derivatives, arylamine derivatives, amino-substituted calcone derivatives, styryl anthracene derivatives, fluorenone derivatives, hydrazone derivatives, stilbene derivatives and silazane derivatives; aromatic tertiary amine compounds, styrylamine compounds, aromatic dimethylidene compounds and porphyrin compounds; anthraquinodimethane derivatives, anthrone derivatives, diphenylquinone derivatives, thiopyrandioxide derivatives, carbodiimide derivatives, fluorenylidenemethane derivatives and distyrylpyrazine derivatives; heterocyclic tetracarboxylic anhydrides such as naphthaleneperylene; phthalocyanine derivatives; metal complexes of 8-quinolinol derivatives; various metal complex polysilane compounds of metal complexes having metalphthalocyanine, benzoxazole or benzothiaole as a ligand; electroconductive macromolecular oligomers such as poly(N-vinylcarbazole) derivatives, aniline copolymers, thiophene oligomers and polythiophene; and macromolecular compounds such as polythiophene derivatives, polyphenylene derivatives, polyphenylenevinylene derivatives and polyfluorene derivatives. Host compounds can be used individually or as a combination of two or more kinds.

Specific compounds shown below can be exemplified.

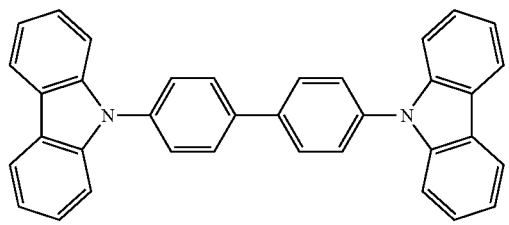

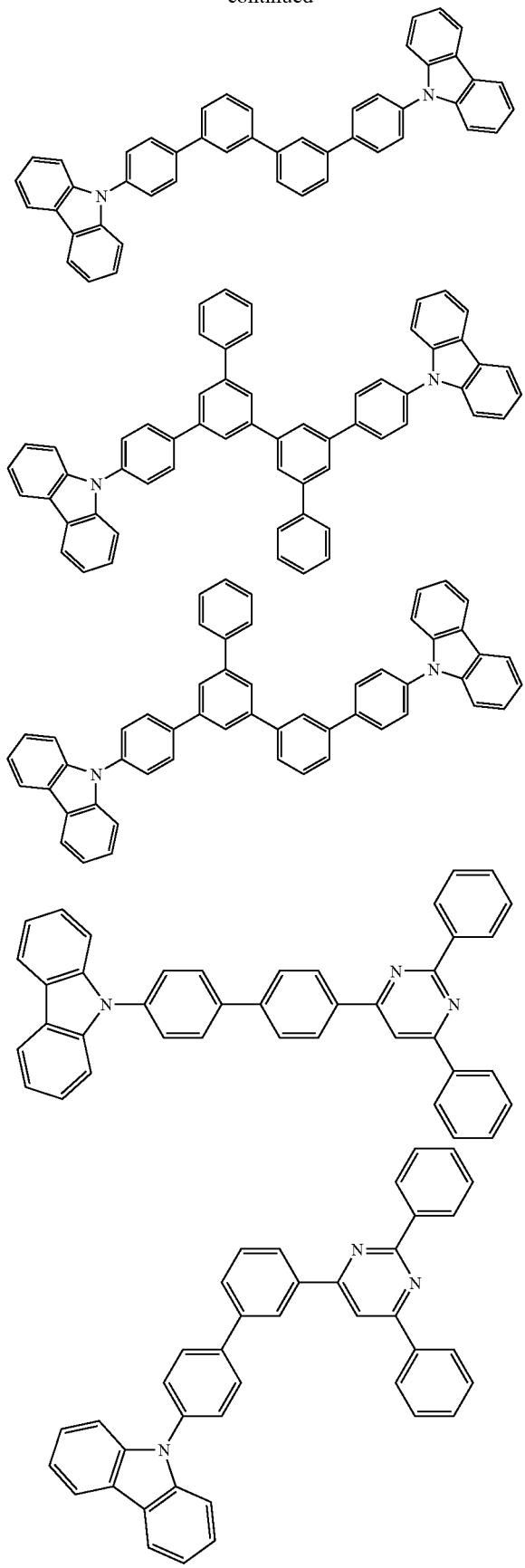

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. As the porphyrin metal complex, a porphyrin platinum complex is preferable. The phosphorescent compounds can be used individually or as a combination of two or more kinds.

There are various ligands forming an ortho-metalated metal complex. Preferable ligands include 2-phenylpyridine derivatives, 7,8-benzoquinoline derivatives, 2-(2-thienyl)pyridine derivatives, 2-(1-naphtyl)pyridine derivatives and 2-phenylquinoline derivatives. These derivatives may have substituents, if necessary. Fluorides and derivatives with a trifluoromethyl group introduced are particularly preferable as a blue dopant. As an auxiliary ligand, preferred are ligands other than the above-mentioned ligands, such as acetylacetonate and picric acid.

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

(Hole-Transporting Layer:Hole-Injecting Layer)

The hole-transporting layer is a layer for helping the injection of holes into the emitting layer so as to transport holes to an emitting region. The hole mobility thereof is large and the ionization energy thereof is usually as small as 5.5 eV or less. Such a hole-transporting layer is preferably made of a material which can transport holes to the emitting layer at a low electric field intensity. The hole mobility of the material is preferably at least $10^{-4}$ cm$^2$/V·sec when an electric field of $10^4$ to $10^6$ V/cm is applied, for example.

Specific examples of materials for a hole-transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712 and 47-25336, JP-A-54-119925, and others), arylamine derivatives (see U.S. Pat. Nos. 3,567,450, 3,240,597, 3,658,520, 4,232,103, 4,175,961 and 4,012,376, JP-B-49-35702 and 39-27577, JP-A-55-144250, 56-119132 and 56-22437, DE1, 110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), aniline copolymers (JP-A-2-282263), and electroconductive high molecular oligomers (in particular thiophene oligomers).

In addition to the hole-transporting layer, in order to help the injection of holes, the hole-injecting layer is provided separately. As the material for the hole-injecting layer, the organic EL material of the invention may be used singly or in combination with other materials. As the other materials, the same materials as used for the hole-transporting layer or the compounds exemplified by the above-mentioned formula (III) can be used. The following can also be used: porphyrin compounds (disclosed in JP-A-63-2956965 and others), and aromatic tertiary amine compounds and styrylamine compounds (see U.S. Pat. No. 4,127,412, JP-A-53-27033, 54-58445, 55-79450, 55-144250, 56-119132, 61-295558, 61-98353 and 63-295695, and others).

The following can also be given as examples: 4,4'-bis(N-(1-naphthyl)-N-phenylamino)biphenyl (NPD), which has in the molecule thereof two condensed aromatic rings, disclosed in U.S. Pat. No. 5,061,569, and 4,4',4"-tris(N-(3-methylphenyl)-N-phenylamino)triphenylamine (MTDATA), wherein three triphenylamine units are linked in a star-burst form, disclosed in JP-A-4-308688.

Inorganic compounds such as p-type Si and p-type SiC as well as aromatic dimethylidene type compounds can also be used as the material of the hole-injecting layer.

The hole-injecting layer or hole-transporting layer can be formed from the above-mentioned compounds by a known method such as vacuum deposition, spin coating, casting or LB technique. The film thickness of the hole-injecting layer and hole-transporting layer is not particularly limited, and is usually from 5 nm to 5 μm. The hole-injecting layer or hole-transporting layer may be a single layer made of one, or two or more of the above-mentioned materials, or may be stacked hole-injecting layers or hole-transporting layers made of different compounds, insofar as the compound of the invention is contained in the hole-transporting region.

An organic semiconductor layer is one type of a hole-transporting layer for helping the injection of holes or electrons into an emitting layer, and is preferably a layer having an electric conductivity of $10^{-10}$ S/cm or more. As the material of such an organic semiconductor layer, electroconductive oligomers such as thiophene-containing oligomers or arylamine-containing oligomers disclosed in JP-A-8-193191, and electroconductive dendrimers such as arylamine-containing dendrimers may be used.

(Electron-Injecting/Transporting Layer)

The electron-injecting/transporting layer is a layer which assists injection of electrons into the emitting layer and transports electrons to the emitting region, and exhibits a high electron mobility. An adhesion-improving layer is formed of a material which exhibits excellent adhesion to the cathode among various electron-injecting layers.

The thickness of the electron-transporting layer is arbitrarily selected in the range of several nanometers to several micrometers. When the electron-transporting layer has a large thickness, it is preferable that the electron mobility be at least $10^{-5}$ cm$^2$/Vs or more at an applied electric field of $10^4$ to $10^6$ V/cm in order to prevent an increase in voltage.

The material used in the electron-injecting layer is preferably a metal complex of 8-hydroxyquinoline or a derivative thereof. As specific examples of the metal complex of 8-hydroxyquinoline and a derivative thereof, metal chelate oxinoid compounds including a chelate of oxine (generally 8-quinolinol or 8-hydroxyquinoline), e.g. tris(8-quinolinol) aluminum, can be used as an electron-injecting material.

An electron-transporting compound of the following formula can be given as the oxadiazole derivative.

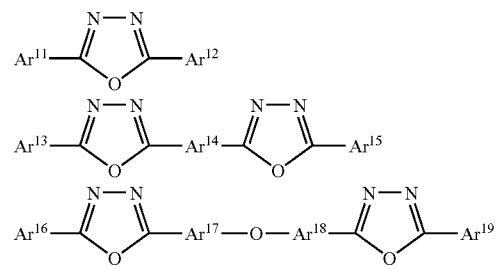

wherein Ar$^{11}$, Ar$^{12}$, Ar$^{13}$, Ar$^{15}$, Ar$^{16}$, and Ar$^{19}$ are independently substituted or unsubstituted aryl groups and may be the same or different. Ar$^{14}$, Ar$^{17}$, and Ar$^{18}$ are substituted or unsubstituted arylene groups and may be the same or different.

As examples of the aryl group, a phenyl group, a biphenyl group, an anthranyl group, a perylenyl group, and a pyrenyl group can be given. As examples of the arylene group, a phenylene group, a naphthylene group, a biphenylene group, an anthranylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron transporting compound is preferably one from which a thin film can be formed.

The following compounds can be given as specific examples of the electron transporting compound.

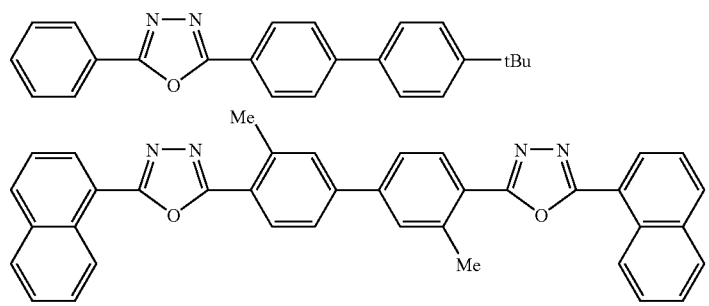

-continued

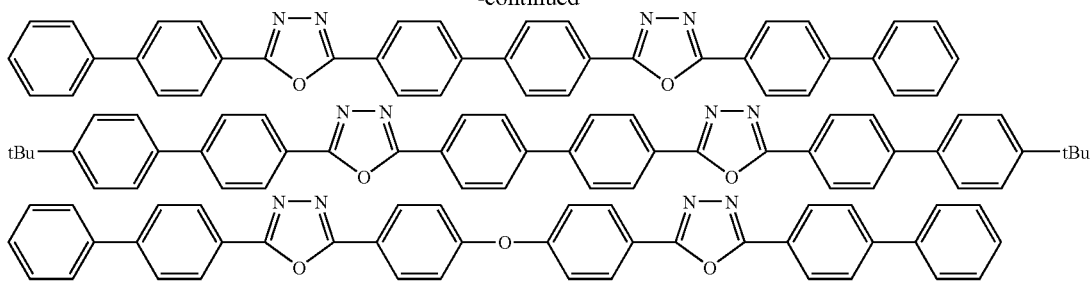

Furthermore, as materials used for the electron-injecting layer and electron-transporting layer, the compounds represented by the following formulas (A) to (F) may be used.

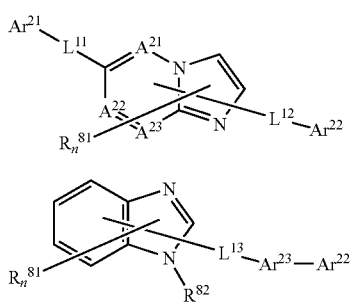

Nitrogen-containing heterocyclic derivatives represented by the formulas (A) and (B) wherein $A^{21}$ to $A^{23}$ are each independently a nitrogen atom or a carbon atom;

$Ar^{21}$ is a substituted or unsubstituted aryl group having 6 to 60 ring carbon atoms or a substituted or unsubstituted heteroaryl group having 3 to 60 ring carbon atoms; $Ar^{22}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms, or a divalent group of these; provided that one of $Ar^{21}$ and $Ar^{22}$ is a substituted or unsubstituted condensed ring group having 10 to 60 ring carbon atoms, a substituted or unsubstituted monohetero condensed ring group having 3 to 60 ring carbon atoms, or a divalent group of these;

$Ar^{23}$ is a substituted or unsubstituted arylene group having 6 to 60 carbon atoms or a substituted or unsubstituted heteroarylene group having 3 to 60 carbon atoms;

$L^{11}$, $L^{12}$, and $L^{13}$ are independently a single bond, a substituted or unsubstituted arylene group having 6 to 60 ring carbon atoms, a substituted or unsubstituted heteroarylene group having 3 to 60 ring carbon atoms or a substituted or unsubstituted fluorenylene group;

$R^{81}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, and n is an integer of 0 to 5, provided that, when n is 2 or more, a plurality of $R^{81}$s may be the same or different; adjacent $R^{81}$s may be bonded to form a carbocyclic aliphatic ring or a carbocyclic aromatic ring;

$R^{82}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms or $-L^{11}-Ar^{21}-Ar^{22}$.

$$HAr-L^{14}-Ar^{24}-Ar^{25} \quad (C)$$

Nitrogen-containing heterocyclic derivatives represented by the formula (C) wherein HAr is a nitrogen-containing heterocycle with 3 to 40 carbon atoms which may have a substituent; $L^{14}$ is a single bond, an arylene group with 6 to 60 carbon atoms which may have a substituent, a heteroarylene group with 3 to 60 carbon atoms which may have a substituent or a fluorenylene group which may have a substituent; $Ar^{24}$ is a divalent aromatic hydrocarbon group with 6 to 60 carbon atoms which may have a substituent; and $Ar^{25}$ is an aryl group with 6 to 60 carbon atoms which may have a substituent or a heteroaryl group with 3 to 60 carbon atoms which may have a substituent.

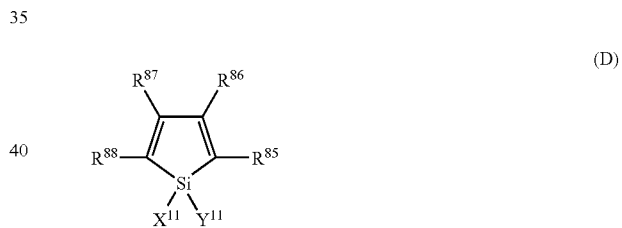

Silacyclopentadiene derivatives represented by the formula (D) wherein $X^{11}$ and $Y^{11}$ are independently a saturated or unsaturated hydrocarbon group having 1 to 6 carbon atoms, an alkoxy group, an alkenyloxy group, an alkynyloxy group, a hydroxy group, a substituted or unsubstituted aryl group, a substituted or unsubstituted heterocycle, or a structure in which $X^{11}$ and $Y^{11}$ bond to each other to form a saturated or unsaturated ring, $R^{85}$ to $R^{88}$ are independently hydrogen, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocycle group, an alkenyl group, an alkynyl group, a nitro group, a formyl group, a nitroso group, a formyloxy group, an isocyano group, a cyanate group, an isocyanate group, a thiocyanate group, an isothiocyanate group, a cyano group, or a structure in which adjacent substituted or unsubstituted rings of $R^{85}$ to $R^{88}$ are condensed.

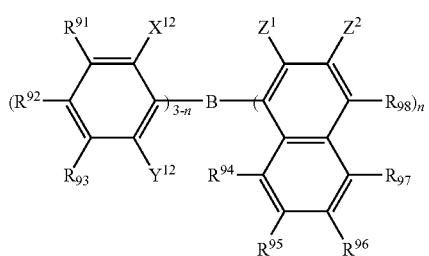
(E)

Borane derivatives represented by the formula (E) wherein $R^{91}$ to $R^{98}$ and $Z^2$ are independently a hydrogen atom, a saturated or unsaturated hydrocarbon group, an aromatic group, a heterocyclic group, a substituted amino group, a substituted boryl group, an alkoxy group, or an aryloxy group; $X^{12}$, $Y^{12}$, and $Z^1$ are independently a saturated or unsaturated hydrocarbon group, an aromatic group, a heterocyclic group, a substituted amino group, an alkoxy group, or an aryloxy group; the substituents of $Z^1$ and $Z^2$ may be bonded to form a condensed ring; and n is an integer of 1 to 3; provided that the $Z^1$s may differ when n is 2 or more, and a case in which n is 1, $X^{12}$, $Y^{12}$, and $R^{92}$ are methyl groups, and $R^{98}$ is a hydrogen atom or a substituted boryl group, and a case in which n is 3 and $Z^1$ is a methyl group are excluded.

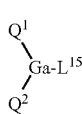
(F)

wherein $Q^1$ and $Q^2$ are independently ligands represented by the following formula (G) and $L^{15}$ is a halogen atom, a substituted or unsubstituted alkyl group, a substituted or unsubstituted cycloalkyl group, a substituted or unsubstituted aryl group, a substituted or unsubstituted heterocyclic group, —OR' (R' is a hydrogen atom, a substituted or unsubstituted alkyl group, a substituted or unsubstituted cycloalkyl group, a substituted or unsubstituted aryl group, or a substituted or unsubstituted heterocyclic group) or a ligand represented by —O—Ga-$Q^3$($Q^4$) ($Q^3$ and $Q^4$ have the same as $Q^1$ and $Q^2$.

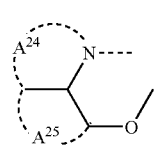
(G)

wherein rings $A^{24}$ and $A^{25}$ are condensed to each other to form a 6-membered aryl ring structure which may have a substituent.

The metal complexes have the strong nature of an n-type semiconductor and large ability of injecting electrons. Further the energy generated at the time of forming a complex is small so that a metal is then strongly bonded to ligands in the complex formed and the fluorescent quantum efficiency becomes large as the emitting material Specific examples of the substituents for the rings $A^{24}$ and $A^{25}$ forming the ligand of the formula (G) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, diethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl)amino group, and bis(acetoxybutyl)amino group, a hydroxyl group, a siloxy group, an acyl group, an carbamoyl group, substituted or unsubstituted carbamoyl groups such as a methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and a cyclohexyl group, aryl groups such as a phenyl group, naphthyl group, biphenyl group, anthryl group, phenanthryl group, fluorenyl group, and pyrenyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triatynyl group, carbazolyl group, furanyl group, thiophenyl group, oxazolyl group, oxadiazolyl group, benzooxazolyl group, thiazolyl group, thiadiazolyl group, benzothiazolyl group, triazolyl group, imidazolyl group, benzimidazolyl group and puranyl, and the like. The above substituents may be bonded to form a six-membered aryl ring or heterocyclic ring.

A preferred embodiment of the invention is a device containing a reducing dopant in an electron-transferring region or in an interfacial region between the cathode and the organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal organic complexes, alkaline earth metal organic complexes, and rare earth metal organic complexes.

More specific examples of the preferred reducing dopants include at least one alkali metal selected from the group consisting of Li (work function: 2.9 eV), Na (work function:

2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). Reducing dopants having a work function of 2.9 eV or less are particularly preferable.

Among these, a more preferable reducing dopant is at least one alkali metal selected from the group consisting of K, Rb and Cs. Even more preferable is Rb or Cs. Most preferable is Cs.

These alkali metals are particularly high in reducing ability. Thus, the addition of a relatively small amount thereof to an electron-injecting zone improves the luminance of the organic EL device and make the lifetime thereof long. As a reducing agent having a work function of 2.9 eV or less, combinations of two or more alkali metals are preferable, and particularly combinations including Cs, such as Cs and Na, Cs and K, Cs and Rb, or Cs, Na and K, are preferable.

The combination containing Cs makes it possible to exhibit the reducing ability efficiently. The luminance of the organic EL device can be improved and the lifetime thereof can be made long by the addition thereof to its electron-injecting zone.

In the invention, an electron-injecting layer made of an insulator or a semiconductor may further be provided between a cathode and an organic layer. By forming the electron-injecting layer, a current leakage can be effectively prevented and electron-injecting properties can be improved.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved.

Specifically preferable alkali metal calcogenides include $Li_2O$, LiO, $Na_2S$, $Na_2Se$ and NaO and preferable alkaline earth metal calcogenides include CaO, BaO, SrO, BeO, BaS and CaSe. Preferable halides of alkali metals include LiF, NaF, KF, LiCl, KCl and NaCl. Preferable halides of alkaline earth metals include fluorides such as $CaF_2$, $BaF_2$, $SrF_2$, $MgF_2$ and $BeF_2$ and halides other than fluorides.

Semiconductors forming an electron-transporting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn.

An inorganic compound forming an electron-transporting layer is preferably a microcrystalline or amorphous insulating thin film. When the electron-transporting layer is formed of the insulating thin films, more uniformed thin film is formed whereby pixel defects such as a dark spot are decreased.

Examples of such an inorganic compound include the above-mentioned alkali metal calcogenides, alkaline earth metal calcogenides, halides of alkali metals, and halides of alkaline earth metals.

(Cathode)

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, magnesium/silver alloy, aluminum/aluminum oxide, aluminum/lithium alloy, indium, and rare earth metals.

This cathode can be formed by making the electrode substances into a thin film by vapor deposition, sputtering or some other method.

In the case where light is emitted from the emitting layer through the cathode, the cathode preferably has a light transmittance of larger than 10%.

The sheet resistance of the cathode is preferably several hundred Ω/□ or less, and the film thickness thereof is usually from 10 nm to 1 μm, preferably from 50 to 200 nm.

(Insulating Layer)

In the organic EL device, pixel defects based on leakage or a short circuit are easily generated since an electric field is applied to the ultrathin film. In order to prevent this, it is preferred to insert an insulative thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, cesium fluoride, cesium carbonate, aluminum nitride, titanium oxide, silicon oxide, germanium oxide, silicon nitride, boron nitride, molybdenum oxide, ruthenium oxide, and vanadium oxide.

A mixture or laminate thereof may be used.

(Example of Fabricating Organic EL Device)

Using the above-mentioned materials, an organic EL device can be fabricated by forming an anode, a hole-injecting layer, a hole-transporting layer, an emitting layer, an electron-injecting layer or the like, followed by formation of a cathode. The organic EL device can be fabricated in the order reverse to the above, i.e., the order from a cathode to an anode.

An example of the fabrication of the organic EL device will be described below which has a structure wherein the following are successively formed on a transparent substrate: anode/hole-injecting layer/hole-transporting layer/emitting layer/electron-transporting layer/cathode.

First, a thin film made of an anode material is formed into a thickness of 1 μm or less, preferably 10 to 200 nm on an appropriate transparent substrate by vapor deposition, sputtering or some other method, thereby forming an anode.

Next, a hole-injecting layer and a hole-transporting layer are formed on this anode. As described above, these layers can be formed by vacuum deposition, spin coating, casting, LB technique, or some other method. Vacuum deposition is preferred since a homogenous film is easily obtained and pinholes are not easily generated.

In the case where the hole-injecting layer and the hole-transporting layer are formed by vacuum deposition, conditions for the deposition vary depending upon the compound used, the desired crystal structure or recombining structure of the hole-injecting layer or hole-transporting layer, and others. In general, the conditions are preferably selected from the following: deposition source temperature of 50 to 450° C., vacuum degree of $10^{-7}$ to $10^{-3}$ torr, vapor deposition rate of 0.01 to 50 nm/second, substrate temperature of −50 to 300° C., and film thickness of 5 nm to 5 μm.

Next, an emitting layer is formed on the hole-transporting layer. The emitting layer can also be formed by making a desired organic luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-transporting layer.

Next, an electron-transporting layer is formed on this emitting layer. Like the hole-transporting layer and the emitting layer, the layer is preferably formed by vacuum vapor deposition because a homogenous film is required. Conditions for the deposition can be selected from conditions similar to those for the hole-transporting layer and the emitting layer.

Lastly, a cathode is stacked thereon to obtain an organic EL device.

The cathode is made of a metal, and vapor deposition or sputtering may be used. However, vapor vacuum deposition is preferred in order to protect underlying organic layers from being damaged when the cathode film is formed.

For the organic EL device fabrication that has been described above, it is preferred that the formation from the anode to the cathode is continuously carried out, using only one vacuuming operation.

The method for forming each of the layers in the organic EL device of the invention is not particularly limited. Specifically the layers can be formed by a known method, such as vacuum deposition, molecular beam deposition (MBE method), or coating method such as dipping, spin coating, casting, bar coating and roll coating using a solution obtained by dissolving a material in a solvent.

The film thickness of each layer constituting the organic layer in the organic EL device of the invention is not particularly limited. In general, defects such as pinholes are easily generated when the film thickness is too small. Conversely, a high applied voltage becomes necessary, leading to low efficiency, when the film thickness is too large. Usually, therefore, the film thickness is preferably in the range of several nanometers to one micrometer.

The organic EL device emits light when applying a voltage between electrodes. If a DC voltage is applied to the organic EL device, emission can be observed when the polarities of the anode and the cathode are positive and negative, respectively, and a DC voltage of 5 to 40 V is applied. When a voltage with an opposite polarity is applied, no electric current flows and hence, emission does not occur. If an AC voltage is applied, uniform emission can be observed only when the cathode and the anode have a positive polarity and a negative polarity, respectively. The waveform of the applied AC may be arbitrary.

A organic EL display apparatus can be produced by arranging a plural of the organic EL devices described above on a substrate.

Figure 2:
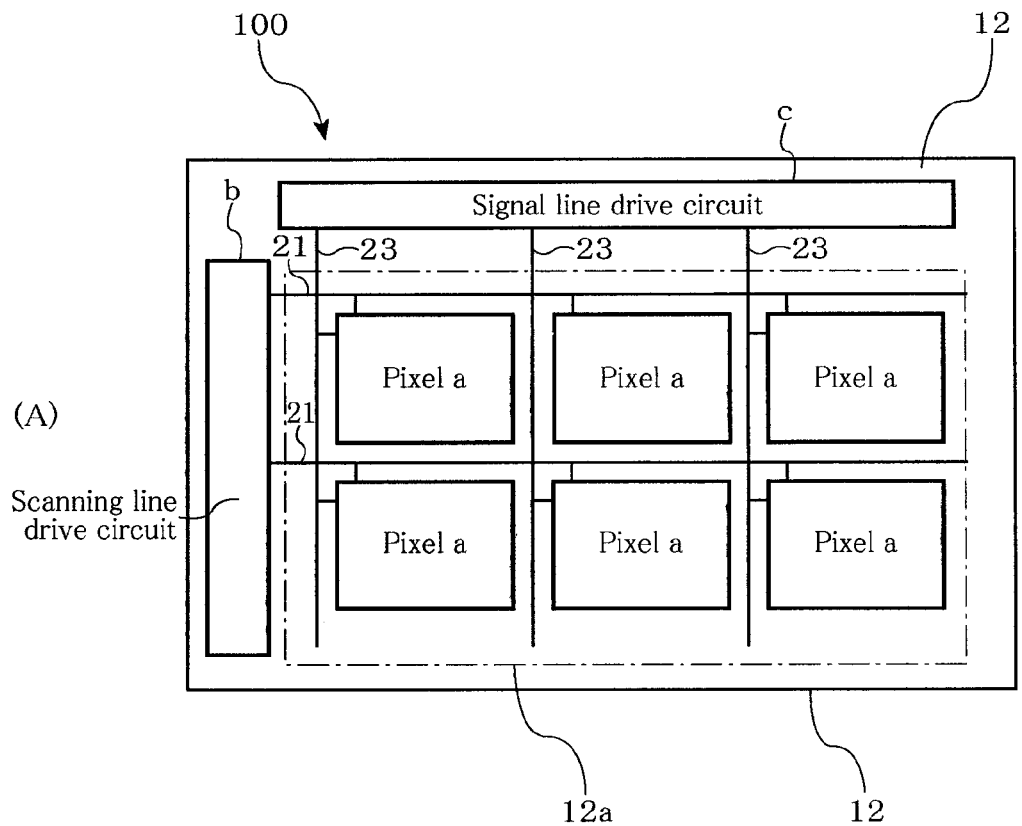
FIG. 2 is a view showing one embodiment of the organic EL display according to the invention; (A) is a schematic diagram and (B) is a diagram of a pixel circuit.
Figure 2:
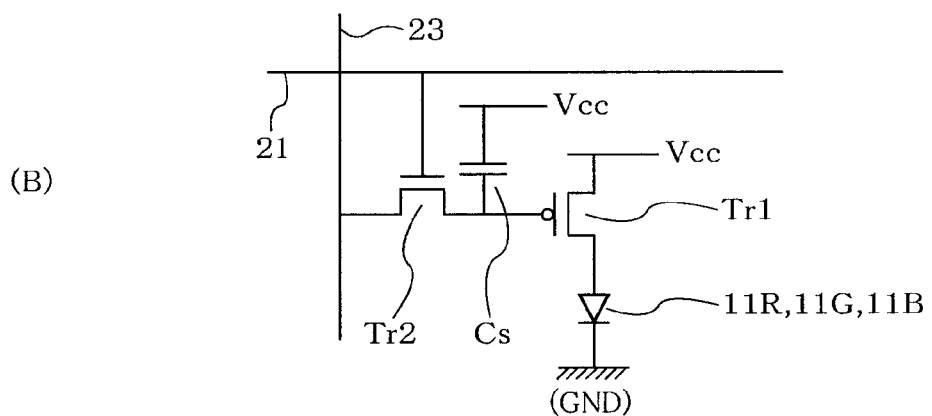

FIG. 2 shows one embodiment of the organic EL display apparatus of the invention. FIG. 2(A) is a schematic configuration diagram, and FIG. 2(B) is a configuration diagram of a pixel circuit. Here, the embodiment will be explained in which the invention is applied to an active-matrix type display apparatus 100 utilizing an organic EL device 11 as an emitting device.

FIG. 2(A) shows that a display area 12*a* and a peripheral area 12*b* thereof are arranged on a substrate 12 of this display apparatus 100. In the display area 12*a*, a plurality of scanning lines 21 and a plurality of signal lines 23 are arranged longitudinally and transversely. A pixel array part is formed in which one pixel a is arranged corresponding to each intersection. Each pixel a has one of organic EL devices 11R, 11G and 11B. In the peripheral area 12*b*, a scanning line drive circuit b for driving the scanning lines 21 and a signal line drive circuit c for supplying an image signal corresponding to luminance information, i.e. input signal, to the signal lines 23 are arranged.

As shown in FIG. 2(B), a pixel circuit arranged in each pixel a comprises one of the organic EL devices 11R, 11G and 11B, a drive transistor Tr1, a write transistor (sampling transistor) Tr2, and a holding capacity Cs, for example. By driving by the scanning line drive circuit b, a written image signal from the signal line 23 through the write transistor Tr2 is held in the holding capacity Cs. Subsequently, a current corresponding to the held signal amount is supplied to each of the organic EL devices 11R, 11G and 11B. The organic EL devices 11R, 11G and 11B emit light with luminances corresponding to the current values.

The above-mentioned constitution of the pixel circuit is just one example. If necessary, a capacity device may be provided in the pixel circuit, or a plurality of transistors may be arranged. Further, in the peripheral area 12*b*, a drive circuit may be added which is necessary for a change in the pixel circuit.

Figure 3:
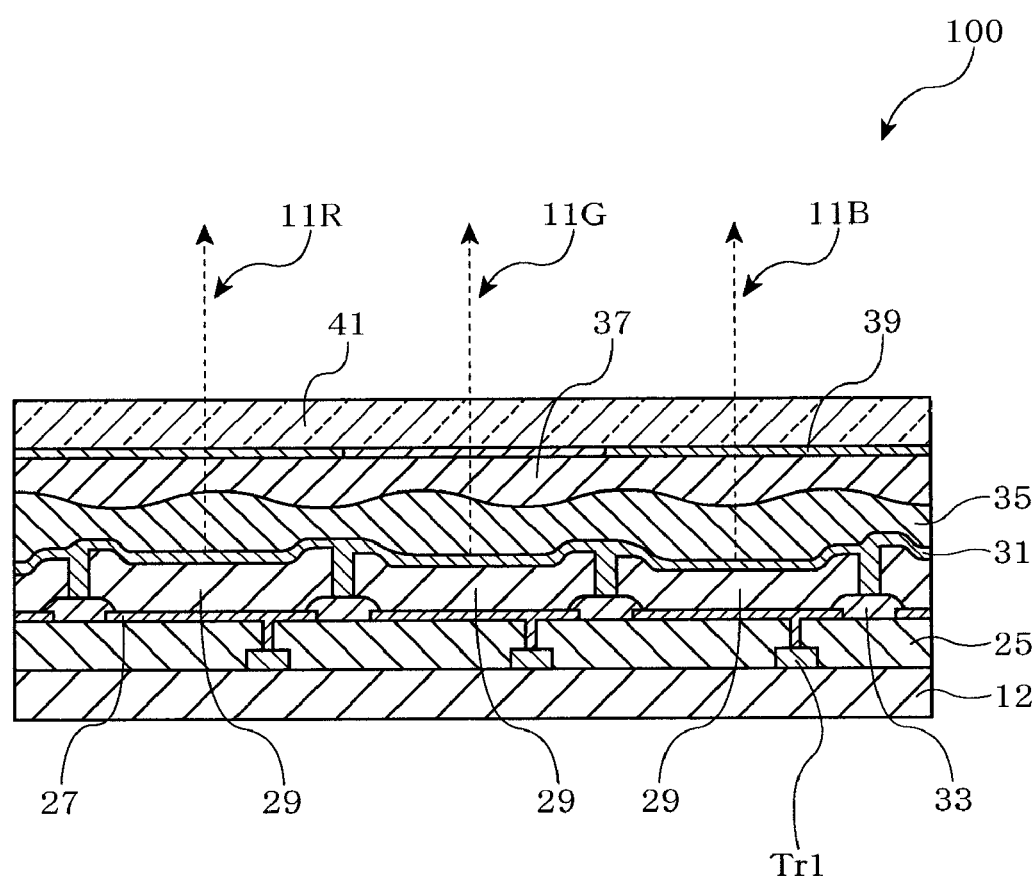
FIG. 3 is a schematic sectional view of main parts of an organic EL display 100.

FIG. 3 shows an example of cross-sectional configuration of main parts in a display area of the display apparatus 100.

On the display area of the substrate 12, where the organic EL devices 11R, 11G and 11B are to be arranged, drive transistors, write transistors, scanning lines and signal lines are arranged to constitute the above-mentioned pixel circuit (see FIG. 2), and an insulating film 25 is provided to cover them.

On the substrate 12 covered with this insulating film 25, the organic EL devices 11R, 11G and 11B are arranged. Each of the organic EL devices 11R, 11G and 11B is formed as a top-emission type device in which light is outcoupled in the direction opposing to the substrate 12.

The anode 27 of each organic EL device 11R, 11G or 11B is patterned in each device. The anode 27 is connected to the drive transistor Tr1 of the corresponding pixel circuit through a connection hole formed on the insulating film 25 covering the surface of the substrate 12.

Each anode 27 is covered in the peripheral part thereof with an insulating film 33. The central part of the anode 27 is exposed in an opening part of the insulating film 33. An organic layer 29 is pattered so as to cover the exposed part of the anode 27, and a cathode 31 is arranged as a common layer covering each organic layer 29.

As shown in FIG. 3, if necessary, subsequently to the cathode 31, a protect layer 35, a adhesive layer 37, a color filter 39 and a sealing substrate 41 may be provided.

The organic layer 29 is composed of a single layer or plural layers containing at least an emitting layer, like the above-mentioned organic EL device.

EXAMPLES

The material for an organic EL device and the organic EL device of the invention will be described in detail referring to the following examples, which should not be construed as limiting the scope of the invention.

The structures of the compounds synthesized or used in the examples are shown below.

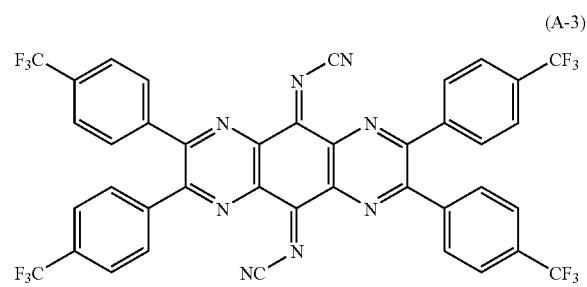

(A-3)

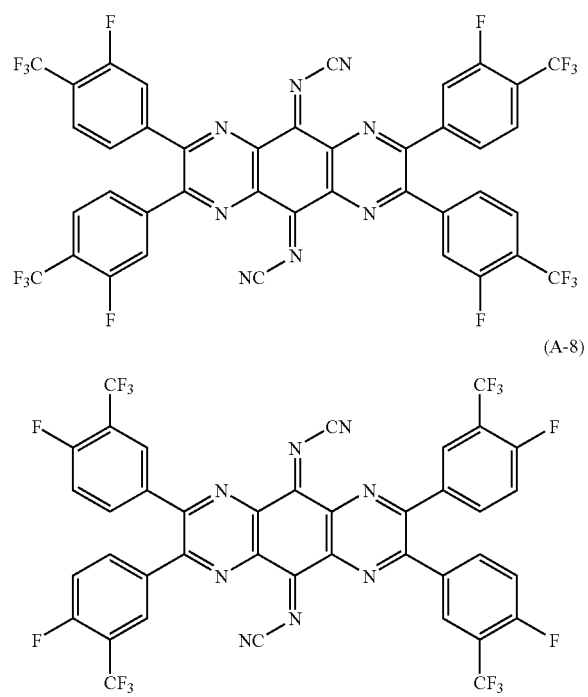
(A-7)
(A-8)
(A-21)
(A-22)
(B-14)
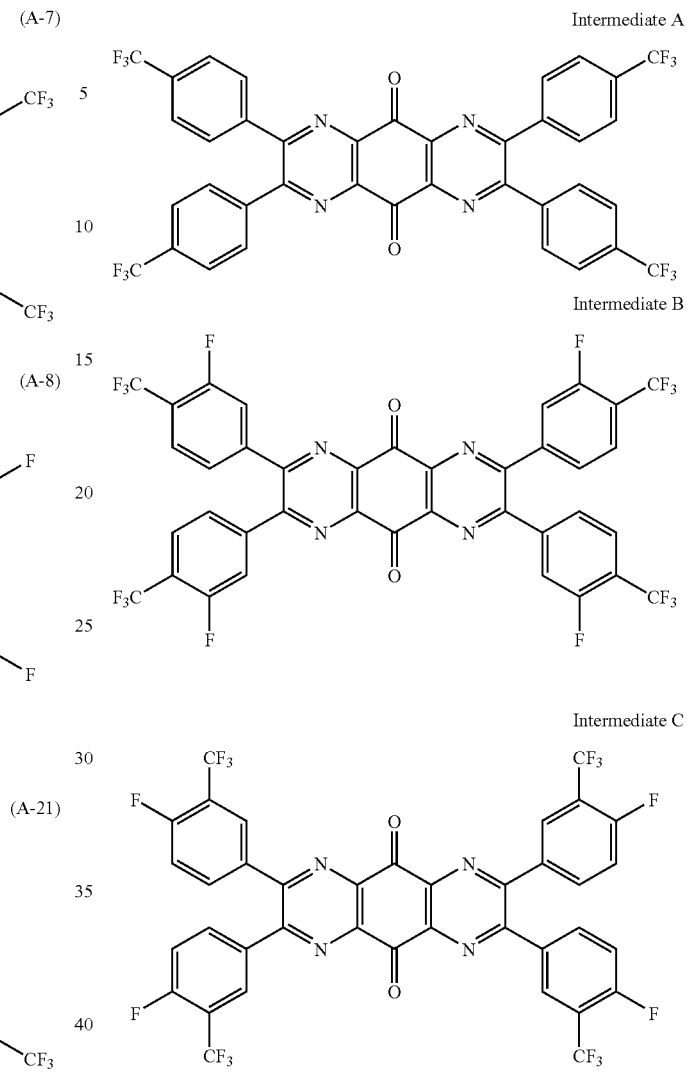
Intermediate A
Intermediate B
Intermediate C
Intermediate D
Intermediate E -continued Intermediate F

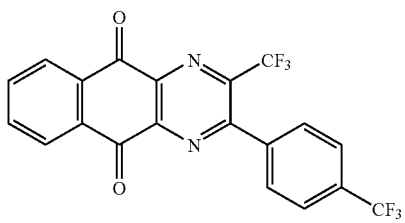

Example 1

Synthesis of Compound (A-3)

(1) Synthesis of Intermediate A 1.6 g of tetraminodiphenoquinone synthesized according to the method described in Justus Liebigs Ann. Chem., 667, 55 to 71 (1963), and 7.0 g of 4,4'-bis(trifluoromethyl)benzyl were added to 50 ml of acetic acid and heated at 80° C. for 3 hours with stirring. After cooling, the reaction solution was concentrated and solid precipitates were filtered and purified by a silica gel column, whereby 2.8 g of intermediate A (yellow solid) was obtained.

As a result of an IR measurement of the compound, the absorption of a carbonyl group was observed at 1705 cm$^{-1}$. Mass spectrometry revealed that the compound had a peak at an M/Z of 788.

(2) Synthesis of Compound (A-3)

1.5 g of intermediate A was stirred and dissolved in 70 ml of methylene chloride. The air atmosphere in the flask was replaced with argon and the solution was cooled to –10° C. or less in a salt-ice bath. 1.4 g of titanium tetrachloride was added to the solution, followed by dripping of a mixture of 4.7 g of bistrimethylsilylcarbodiimide and 20 ml of methylene chloride. After the completion of dripping, the cooling was continued for 1 hour. Thereafter, the solution was stirred for 5 hours at room temperature. An orange solid precipitate was filtered and washed with methanol.

The compound was subjected to sublimation and purification at 300° C., whereby 0.7 g of orange solid of compound (A-3) was obtained (sublimation yield: 60%).

As a result of an IR measurement of the compound, the absorption of a carbonyl group disappeared and the absorption of a cyano group was observed at 2166 cm$^{-1}$. Mass spectrometry revealed that the compound had a peak at an M/Z of 836.

The compound was then dissolved in acetonitrile in concentration of 0.01 mol/l. A reduction potential was measured with a cyclic voltammetry at a sweep rate of 0.1 V/s using tetrabutylammonium perchlorate (TBAP) as a supporting electrode and a silver-silver chloride electrode as a reference electrode. When the first oxidation potential of ferrocene (hereinafter referred to as "Fc") as a standard substance was used for a standard, the reduction potential of compound (A-3) was –0.25V (vs Fc$^+$/Fc).

As a result of heat analysis (Thermogravimetry/Differential Thermal Analysis (TG/DTA)) of the orange solid which had been subjected to sublimation and purification, 1% weight loss temperature was 360° C.

Example 2

Synthesis of Compound (A-7)

(1) Synthesis of Intermediate B

Intermediate B was obtained in the same manner as the synthesis of intermediate A in Example 1, except that 7.5 g of 4,4'-difluoro-3,3'-bistrifluoromethylbenzyl was used instead of 4,4'-bistrifluoromethylbenzyl.

As a result of an IR measurement of the compound, the absorption of a carbonyl group was observed at 1705 cm$^{-1}$. Mass spectrometry revealed that the compound had a peak at an M/Z of 860.

(2) Synthesis of Compound (A-7)

1.0 g of orange solid of compound (A-8) was obtained (sublimation yield: 90%) in the same manner as the synthesis of compound (A-3) in Example 1, except that 1.6 g of intermediate B was used instead of intermediate A.

As a result of an IR measurement of the compound, the absorption of a carbonyl group disappeared and the absorption of a cyano group was observed at 2155 cm$^{-1}$. Mass spectrometry revealed that the compound had a peak at an M/Z of 908.

The reduction potential of the compound was measured in the same manner as Example 1. The reduction potential was –0.20V (vs Fc$^+$/Fc).

Example 3

Synthesis of Compound (A-8)

(1) Synthesis of Intermediate C

Intermediate C was obtained in the same manner as the synthesis of intermediate A in Example 1, except that 7.5 g of 4,4'-difluoro-3,3'-bistrifluoromethylbenzyl was used instead of 4,4'-bistrifluoromethylbenzyl.

As a result of an IR measurement of the compound, the absorption of a carbonyl group was observed at 1705 cm$^{-1}$. Mass spectrometry revealed that the compound had a peak at an M/Z of 860.

(2) Synthesis of Compound (A-8)

0.6 g of orange solid of compound (A-8) was obtained (sublimation yield: 60%) in the same manner as the synthesis of compound (A-3) in Example 1, except that 1.6 g of intermediate C was used instead of intermediate A.

As a result of an IR measurement of the compound, the absorption of a carbonyl group disappeared and the absorption of a cyano group was observed at 2155 cm$^{-1}$. Mass spectrometry revealed that the compound had a peak at an M/Z of 908.

The reduction potential of the compound was measured in the same manner as Example 1. The reduction potential was –0.25V (vs Fc$^+$/Fc).

Example 4

Synthesis of Mixture of Compound (A-21) and Compound (A-22)

(1) Synthesis of Mixture of Intermediate D and Intermediate E 3.6 g of 3,3,3-trifluoro-1-(4-(trifluoromethyl)phenyl)propane-1,2-dione monohydrate synthesized referring to Journal of Organic Chemistry, Kamitori et al., vol. 53, page 129, 1988 and 1.1 g of tetraminobenzoquinone were added to 45 ml of acetic acid and heated at 80° C. for 3 hours with stirring. After cooling, the reaction solution was concentrated and solid precipitates were filtered and purified by a silica gel column, whereby 3.1 g of a mixture of intermediate D and intermediate E (yellow solid) was obtained.

As a result of an IR measurement of the compound, the absorption of a carbonyl group was observed at 1717 cm$^{-1}$. Mass spectrometry revealed that the compound had a peak at an M/Z of 636.

(2) Synthesis of Mixture of Compound (A-21) and Compound (A-22)

3.1 g of the mixture of intermediate D and intermediate E was stirred and dissolved in 50 ml of methylene chloride. The air atmosphere in the flask was replaced with argon and the solution was cooled to −10° C. or less in a salt-ice bath. 3.5 g of titanium tetrachloride was added to the solution, followed by dripping of a mixture of 12 g of bistrimethylsilylcarbodiimide and 20 ml of methylene chloride. After the completion of dripping, the cooling was continued for 1 hour. Thereafter the solution was stirred for 5 hours at room temperature. An orange precipitate was filtered and washed with methanol.

The compound was subjected to sublimation and purification at 260° C., whereby 1.3 g of orange solid of a mixture of compound (A-21) and compound (A-22) was obtained.

As a result of an IR measurement of the compound, the absorption of a cyano group was observed at 1791 cm$^{-1}$. Mass spectrometry revealed that the compound had a peak at an M/Z of 684.

The reduction potential of the compound was measured in the same manner as Example 1. The reduction potential was 0.3V (vs Fc$^+$/Fc).

Example 5

Synthesis of Compound (B-14)

(1) Synthesis of Intermediate F

The synthesis was performed in the same manner as Example 4(1), except that 1.2 of 2,3-diamino-1,4-naphtoquinone was used instead of tetraminobenzoquinone, the amount of 3,3-trifluoro-1-(4-(trifluoromethyl)phenyl)propane-1,2-dione monohydrate was changed to 1.6 g and the amount of acetic acid was changed to 40 ml.

As a result of an IR measurement of the compound, the absorption of a carbonyl group was observed at 1715 cm$^{-1}$. Mass spectrometry revealed that the compound had a peak at an M/Z of 422.

(2) Synthesis of Compound (B-14)

The synthesis was performed in the same manner as Example 4(2), except that 2.1 g of intermediate F was used instead of the mixture of intermediate D and intermediate E. The sublimation temperature was 220° C.

As a result of an IR measurement of the compound, the absorption of a cyano group was observed at 1790 cm$^{-1}$. Mass spectrometry revealed that the compound had a peak at an M/Z of 470.

The reduction potential of the compound was measured in the same manner as Example 1. The reduction potential was 0.1V (vs Fc$^+$/Fc).

Comparative Example 1

Synthesis of Compound (F-1)

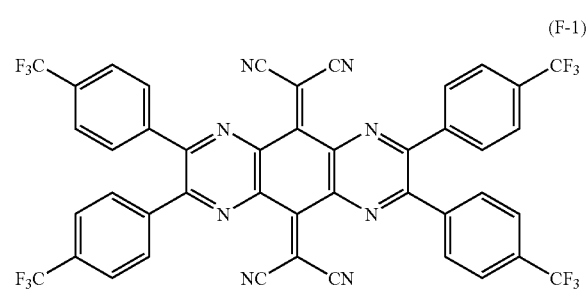

(F-1)

2.5 g of intermediate A synthesized in Example 1 and 0.6 g of malononitrile were mixed with 70 ml of methylene chloride and under a nitrogen atmosphere, 2.5 g of titanium tetrachloride was dripped to the solution while cooling in an ice bath for 20 minutes. Then, 20 ml of pyridine was dripped to the solution for 20 minutes. After stirring at room temperature for 5 hours, 50 ml of 10% hydrochloric acid solution was added and methylene chloride was distilled of under a reduced pressure, followed by filtering and drying of a precipitate. The precipitate was recrystallized from acetonitrile, followed by sublimation and purification at 300° C., whereby 0.3 g of compound (F-1) was obtained (sublimation yield: 20%).

As a result of an IR measurement of the compound, the absorption of a cyano group was observed at 2218 cm$^{-1}$ and the absorption of a carbonyl group at 1705 cm$^{-1}$ disappeared. Mass spectrometry revealed that the compound had a peak at an M/Z of 684.

As a result of the heat analysis (Thermogravimetry/Differential Thermal Analysis (TG/DTA)) of the orange solid which had been subjected to sublimation and purification, 1% weight loss temperature was 345° C.

These results suggested that compound (A-3) synthesized in Example 1 was improved in sublimation and heat resistance by containing a cyanoimine structure.

Organic Electroluminescent Device

Example 6

A grass substrate of 25 mm by 75 mm by 1.1 mm thick with an ITO transparent electrode (GEOMATEC CO., LTD.) was subjected to ultrasonic cleaning with isopropyl alcohol for 5 minutes, and cleaned with ultraviolet rays and ozone for 30 minutes.

The cleaned glass substrate having the transparent electrode lines was then secured to a substrate holder of an apparatus for vacuum deposition. First, compound (A-3) synthesized in Example 1 and the compound represented by the following formula (C-1) were deposited onto the surface of the glass substrate on which the transparent electrode lines were formed so as to cover the transparent electrodes, thereby forming a 60 nm-thick film at a molar ratio of compound (A-3) and the compound (C-1) of 2:98. The mixture film functioned as a hole-injecting layer.

Subsequently, a 20 nm-thick film of the compound represented by the following formula (HTM-1) was formed on the mixture film. The film functioned as a hole-transporting layer.

Further, EM1 was deposited to form a 40 nm-thick film. Simultaneously, the following amine compound D1 having a styryl group as a luminescent molecule was deposited such that the weight ratio of EM1 and D1 was 40:2. The film functioned as an emitting layer.

Alq was deposited thereon to form a 10 nm-thick film. The film functioned as an electron-injecting layer. Then, Li as a reductive dopant (Li source: manufactured by SAES Getters Co., Ltd.) and Alq were co-deposited, whereby an Alq:Li film (film thickness: 10 nm) was formed as an electron-injecting layer (cathode). Metal aluminum was deposited on the Alq:Li film to form a metallic cathode, whereby an organic EL device was fabricated.

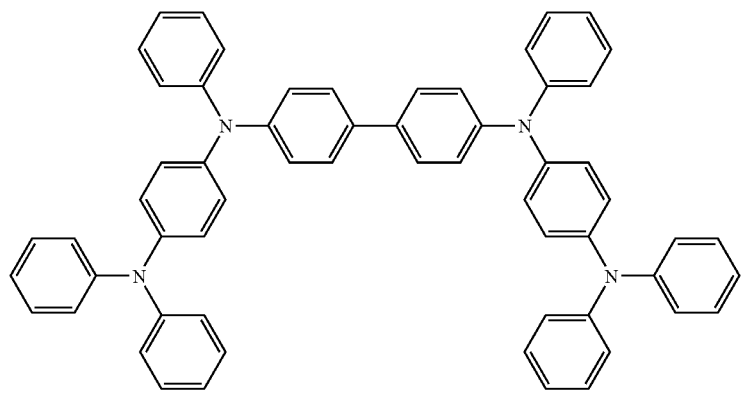
(C-1)
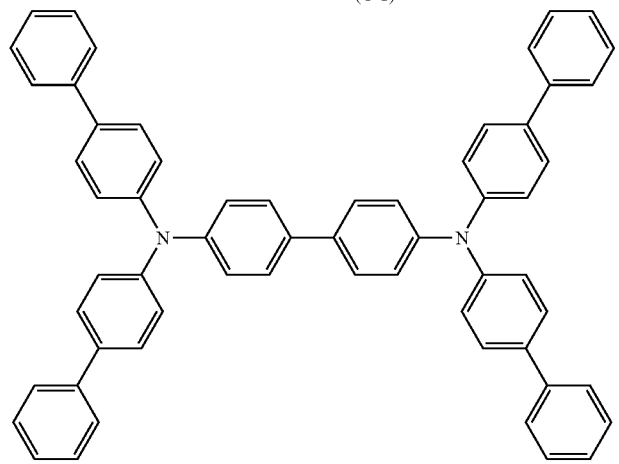
(HTM-1)
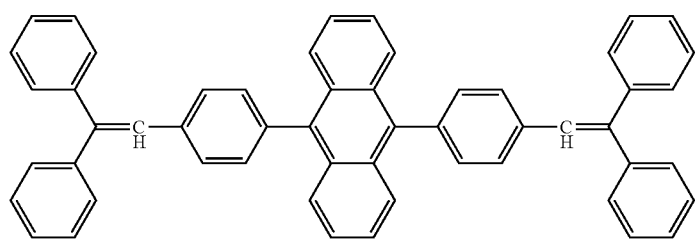
(EM1)
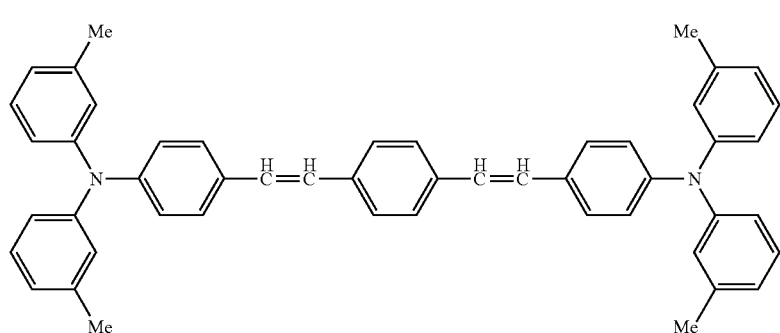
(D1)
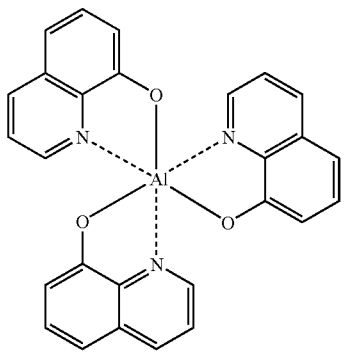
Alq The organic EL device was evaluated by measuring a driving voltage at a current density of 10 mA/cm² and a half life of luminescence at an initial luminance of 1,000 nits at room temperature with DC constant current driving. The results obtained are shown in Table 1.

Example 7

An organic EL device was fabricated and evaluated in the same manner as in Example 6, except that the hole-injecting layer was formed using the compound (A-8) synthesized in Example 3 singly. The results are shown in Table 1.

Example 8

An organic EL device was fabricated and evaluated in the same manner as in Example 6, except that the hole-injecting layer was formed using the mixture of compound (A-21) and compound (A-22) synthesized in Example 4 instead of compound (A-8), the thickness thereof was changed to 10 nm, and the thickness of the hole-transporting layer (HTM-1) was changed to 70 nm. The results are shown in Table 1.

Example 9

An organic EL device was fabricated and evaluated in the same manner as in Example 1, except that the hole-injecting layer was formed using compound (B-14) synthesized in Example 5 instead of compound (A-3). The results are shown in Table 1.

Comparative Example 2

An organic EL device was fabricated and evaluated in the same manner as in Example 6, except that the hole-injecting layer was formed using compound (C-1) singly.
The results are shown in Table 1.

TABLE 1

| | Material of Hole-injecting layer | Driving voltage (V) | Half life (hr) |
|---|---|---|---|
| Example 6 | Formula (A-3) Formula (C-1) | 6.1 | 7,800 |
| Example 7 | Formula (A-8) | 6.4 | 8,700 |
| Example 8 | Formula (A-21) Formula (A-22) | 5.8 | 7,000 |
| Example 9 | Formula (B-14) | 5.9 | 6,500 |
| Comparative Example 2 | Formula (C-1) | 6.6 | 5,000 |

In the following Examples 10 and 11, and Comparative Examples 3 and 4, the device 1 of top-emission type (FIG. 1) wherein an anode was reflective electrode was fabricated.

Example 10

An anode 10 was formed from an aluminum alloy (thickness: about 100 nm) on a glass substrate of 30 mm by 30 mm and the area other than an emission area of 2 mm by 2 mm was masked with an insulating film (not shown in the drawing) by SiO₂ deposition to fabricate a cell for an organic EL device.
Next, a hole-injecting layer 20 with a thickness of 10 nm was formed from compound (A-3) shown in Example 1 by vacuum deposition.
Subsequently, as a hole-transporting layer 30, a 10 nm-thick film of above mentioned HTM-1 was formed (deposition rate: 0.2 to 0.4 nm/sec) thereon. HTM-1 was a hole-transporting material.

Further, as an emitting layer 40, the following compound (EM2) as a host and compound (D-29) as a dopant were vacuum-deposited such that the dopant concentration was 5% in term of a film thickness ratio to form a 26 nm-thick film.

(EM2)

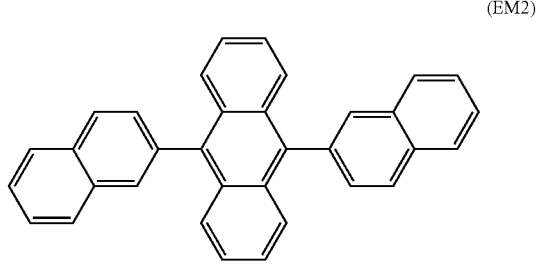

Next, a 10 nm-thick film of Alq was formed (deposition rate: 0.1 nm/sec) by vacuum deposition as an electron-transporting layer 50.
After forming layers from the hole-injecting layer 20 to the electron-transporting layer 50 as mentioned above, an about 0.3 nm-thick film of LiF was formed (deposition rate: to 0.01 nm/sec) as the first layer of cathode and a 10 nm-thick film of MgAg was formed as the second layer of cathode by vacuum deposition to form a cathode 60 of two-layer structure.
The organic EL device was evaluated by measuring a driving voltage and a luminous efficiency at a current load of 10 mA/cm². The results obtained are shown in Table 2.

TABLE 2

| | Material of Hole-injecting layer | Driving voltage (V) | Luminous efficiency (Cd/A) |
|---|---|---|---|
| Example 10 | Formula (A-3) | 6.1 | 2.2 |
| Example 11 | Formula (A-8) | 6.0 | 2.3 |
| Comparative Example 3 | Formula (C-1) | 15.6 | 0.2 |
| Comparative Example 4 | Intermediate A | 13.9 | 0.3 |

Example 11

An organic EL device was fabricated and evaluated in the same manner as in Example 6, except that compound (A-8) synthesized in Example 3 was used as the hole-injecting layer 20 instead of compound (A-3). The results are shown in Table 2.

Comparative Example 3

An organic EL device was fabricated and evaluated in the same manner as in Example 10, except that compound (C-1) was used as the hole-injecting layer 20 instead of compound (A-3). The results are shown in Table 2.

Comparative Example 4

An organic EL device was fabricated and evaluated in the same manner as in Example 10, except that intermediate A synthesized in Example 1 was used as the hole-injecting layer 20 instead of compound (A-3). The results are shown in Table 2.

In Table 2, comparing Comparative Examples 3 and 4 to Examples 10 and 11, the voltage significantly increased and the current efficiency decreased to one tenth or less. As seen in Table 2, the invention can lower power consumption.

INDUSTRIAL APPLICABILITY

The imine derivatives of the invention can be used as a material for organic electronic devices including an organic solar cell, an organic TFT, an organic EL, etc.

The material for an organic EL device of the invention is suitable as constituent materials of an organic EL device, in particular, a material for a hole transporting layer and a hole injecting layer. Further, the material of the invention can be used as a carrier transporting material for an electron photoreceptor. The organic EL device or display of the invention can be suitably used as a light source such as a planar emitting body and backlight of a display, a display part of a portable phone, PDA, a car navigator, or an instruction panel of an automobile, an illuminator, and the like.

The contents of the above-described documents are herein incorporated by reference in its entirety.

The invention claimed is:

1. A material for an organic electroluminescent device comprising an imine derivative represented by the following formula (Ia) or (Ib),

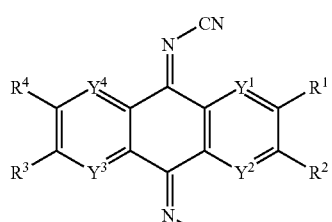

(Ia)

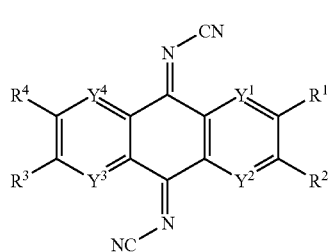

(Ib)

wherein $Y^1$ to $Y^4$ are independently a carbon atom or a nitrogen atom; $R^1$ to $R^4$ are independently hydrogen, an alkyl group, an aryl group, a heterocycle, a halogen atom, a fluoroalkyl group or a cyano group; and $R^1$ and $R^2$, or $R^3$ and $R^4$ may be bonded together to form a ring.

2. The material for an organic electroluminescent device according to claim 1 wherein the imine derivative is represented by the following formula (IIa) or (IIb),

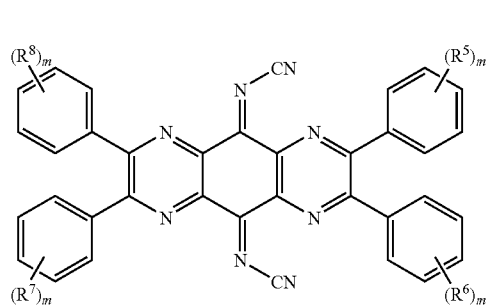

(IIa)

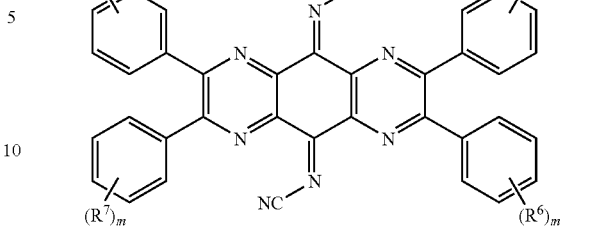

(IIb)

wherein $R^5$ to $R^8$ are independently hydrogen, an alkyl group, fluorine, a fluoroalkyl group or a cyano group; provided that at least one of $R^5$ to $R^8$ is fluorine or a fluoroalkyl group; and ms are independently an integer of 1 to 5.

3. The material for an organic electroluminescent device according to claim 1 wherein the reduction potential of an acetonitrile solution is −1.0V (vs $Fc^+/Fc$ wherein Fc represents ferrocene) or more.

4. The material for an organic electroluminescent device according to claim 1 which is a hole-injecting material.

5. An organic electroluminescent device comprising an organic layer between an anode and a cathode wherein the organic layer comprises the material for an organic electroluminescent device according claim 1.

6. An organic electroluminescent device comprising an organic layer between an anode and a cathode,
wherein the organic layer is a thin-layer stack comprising a hole-injecting layer, a hole-transporting layer, an emitting layer and an electron-transporting layer in sequential order from the anode; and
the hole-injecting layer comprises the material for an organic electroluminescent device according claim 1.

7. The organic electroluminescent device according to claim 6 wherein the hole-injecting layer further comprises a phenylenediamine compound represented by the following formula (III);

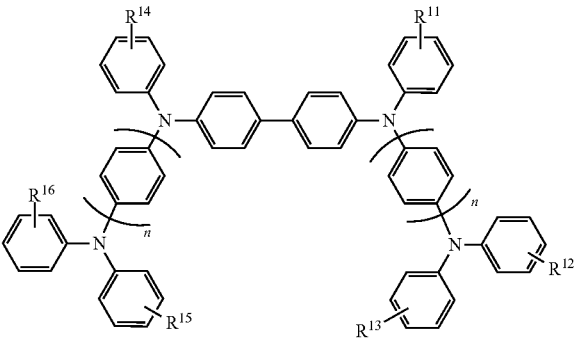

(III)

wherein $R^{11}$ to $R^{16}$ are independently hydrogen, a halogen atom, a trifluoromethyl group, an alkyl group, an aryl group or a heterocycle; $R^{11}$ to $R^{16}$ may each form a naphthalene skeleton, a carbazole skeleton, or a fluorene skeleton with its bonding phenyl group; and n represents 1 or 2.

8. The organic electroluminescent device according to claim 5 wherein the anode comprises a metal formed of aluminum or an aluminum alloy.

9. The organic electroluminescent device according to claim 8 wherein the anode comprises a stack of the metal formed of aluminum or an aluminum alloy, and a metal oxide or nitride.

10. An imine derivative represented by the following formula (IIa) or (IIb),

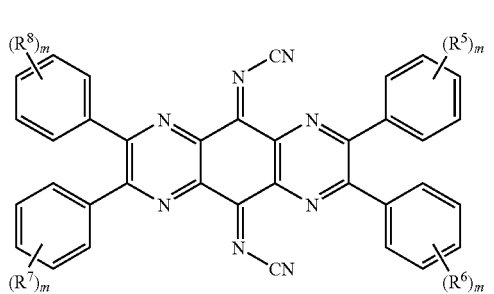

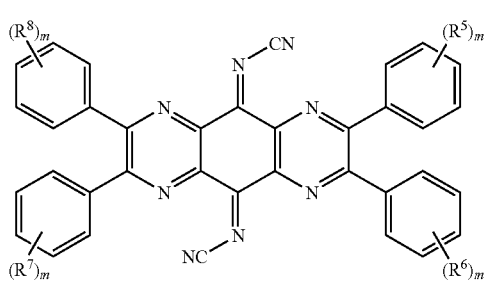

wherein $R^5$ to $R^8$ are independently hydrogen, an alkyl group, fluorine, a fluoroalkyl group or a cyano group; provided that at least one of $R^5$ to $R^8$ is a fluorine or a fluoroalkyl group; and ms are independently an integer of 1 to 5.

11. An organic electroluminescent display wherein a plurality of organic electroluminescent devices in which an anode, an organic layer comprising an emitting layer and a transparent cathode are stacked in sequential order are arranged on a substrate, and
the organic layer comprises an imine derivative represented by the following formula (Ia) or (Ib),

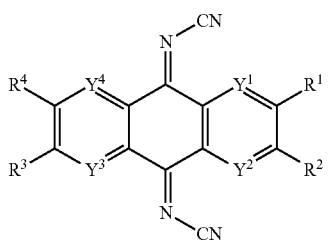

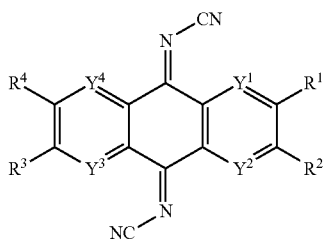

wherein $Y^1$ to $Y^4$ are independently a carbon atom or a nitrogen atom; $R^1$ to $R^4$ are independently hydrogen, an alkyl group, an aryl group, a heterocycle, a halogen atom, a fluoroalkyl group or a cyano group; and $R^1$ and $R^2$, or $R^3$ and $R^4$ may be bonded together to form a ring.

12. An organic electroluminescent display wherein a plurality of organic electroluminescent devices in which an anode, an organic layer comprising an emitting layer and a transparent cathode are stacked in sequential order are arranged on a substrate, and
the organic layer comprises an imine derivative represented by the following formula (IIa) or

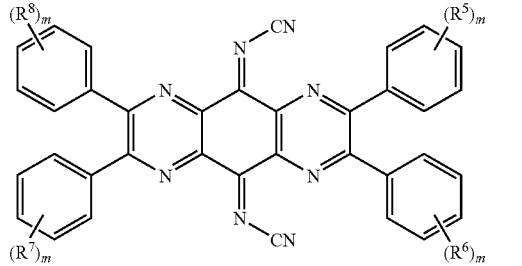

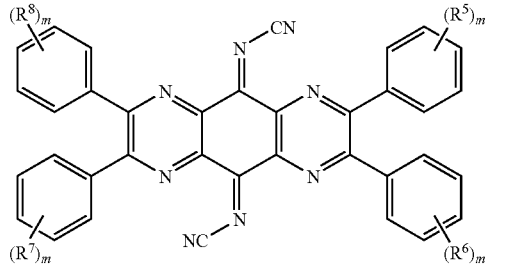

wherein $R^5$ to $R^8$ are independently hydrogen, an alkyl group, fluorine, a fluoroalkyl group or a cyano group; provided that at least one of $R^5$ to $R^8$ is a fluorine or a fluoroalkyl group; and ms are independently an integer of 1 to 5.

13. The organic electroluminescent display according to claim 11 wherein the anode comprises a metal formed of aluminum or an aluminum alloy.

14. The organic electroluminescent display according to claim 13 wherein the anode comprises a stack of the metal formed of aluminum or an aluminum alloy, and a metal oxide or nitride.

15. The organic electroluminescent display according to claim 12 wherein the anode comprises a metal formed of aluminum or an aluminum alloy.

16. The organic electroluminescent display according to claim 15 wherein the anode comprises a stack of the metal formed of aluminum or an aluminum alloy, and a metal oxide or nitride.

* * * * *

UNITED STATES PATENT AND TRADEMARK OFFICE
CERTIFICATE OF CORRECTION

| | |
|---|---|
| PATENT NO. | : 8,044,390 B2 |
| APPLICATION NO. | : 12/601808 |
| DATED | : October 25, 2011 |
| INVENTOR(S) | : Chishio Hosokawa et al. |

It is certified that error appears in the above-identified patent and that said Letters Patent is hereby corrected as shown below:

IN THE CLAIMS:

Col. 56, claim 12, line 12, "formula (IIa) or" should be --formula (IIa) or (IIb)--.

Signed and Sealed this
Seventh Day of February, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 8,044,390 B2 |
| APPLICATION NO. | : 12/601808 |
| DATED | : October 25, 2011 |
| INVENTOR(S) | : Chishio Hosokawa et al. |

It is certified that error appears in the above-identified patent and that said Letters Patent is hereby corrected as shown below:

On the Title Page: Item (22), PCT Filed: "May 21, 2007" should be --May 21, 2008--.

Signed and Sealed this
Seventeenth Day of April, 2012

David J. Kappos
*Director of the United States Patent and Trademark Office*